United States Patent
Carroll, II et al.

(10) Patent No.: US 8,361,112 B2
(45) Date of Patent: Jan. 29, 2013

(54) SURGICAL SUTURE ARRANGEMENT

(75) Inventors: Kempton K. Carroll, II, Cincinnati, OH (US); James T. Spivey, Cincinnati, OH (US); Duane A. Linenkugel, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1048 days.

(21) Appl. No.: 12/163,255

(22) Filed: Jun. 27, 2008

(65) Prior Publication Data

US 2009/0326561 A1    Dec. 31, 2009

(51) Int. Cl.
*A61B 17/04* (2006.01)

(52) U.S. Cl. ........ 606/232; 606/139; 606/185; 606/198; 606/144; 606/223

(58) Field of Classification Search .................. 606/144, 606/148, 139, 198, 185, 232; 604/60; 600/106
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker at al. |
| 2,938,382 A | 5/1960 | De Graaf |
| 2,952,206 A | 9/1960 | Becksted |
| 3,069,195 A | 12/1962 | Buck |
| 3,170,471 A | 2/1965 | Schnitzer |

(Continued)

FOREIGN PATENT DOCUMENTS

| | | |
|---|---|---|
| AU | 666310 B2 | 2/1996 |
| DE | 3008120 A1 | 9/1980 |

(Continued)

OTHER PUBLICATIONS

Written Opinion for PCT/US2009/047599, Sep. 9, 2009 (9 pages).

(Continued)

*Primary Examiner* — Vy Q Bui

(57) ABSTRACT

A surgical instrument may comprise a shaft having proximal and distal ends defining an axis therebetween. The shaft may be flexible and sized for insertion into the working channel of a flexible endoscope. The shaft may be configured to be used in conjunction with various suture anchor applicators. One suture anchor applicator may have a first tube with a first channel and a tissue penetrating tip. The first channel may be adapted to retain a second tube. The second tube may have a second channel and a blunt tip. The second channel may be adapted to retain at least one suture anchor and may include an exit port adapted for ejecting suture anchors. An alternative suture anchor applicator may comprise a first tube and a second tube with a tissue penetrating tip. The second channel is adapted to retain at least one suture anchor.

7 Claims, 16 Drawing Sheets

U.S. PATENT DOCUMENTS

| | | |
|---|---|---|
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |

| Patent | Date | Inventor |
|---|---|---|
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,443,463 A | 8/1995 | Stern et al. |
| 5,445,638 A | 8/1995 | Rydell et al. |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,536,248 A | 7/1996 | Weaver et al. |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,824,071 A | 10/1998 | Nelson et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |

| | | | | | | |
|---|---|---|---|---|---|---|
| 5,882,344 A | 3/1999 | Stouder, Jr. | | 6,159,200 A | 12/2000 | Verdura et al. |
| 5,893,846 A | 4/1999 | Bales et al. | | 6,165,184 A | 12/2000 | Verdura et al. |
| 5,893,874 A | 4/1999 | Bourque et al. | | 6,168,570 B1 | 1/2001 | Ferrera |
| 5,893,875 A | 4/1999 | O'Connor et al. | | 6,168,605 B1 | 1/2001 | Measamer et al. |
| 5,899,919 A | 5/1999 | Eubanks, Jr. et al. | | 6,170,130 B1 | 1/2001 | Hamilton et al. |
| 5,902,254 A | 5/1999 | Magram | | 6,179,776 B1 | 1/2001 | Adams et al. |
| 5,904,702 A | 5/1999 | Ek et al. | | 6,179,837 B1 | 1/2001 | Hooven |
| 5,908,420 A | 6/1999 | Parins et al. | | 6,183,420 B1 | 2/2001 | Douk et al. |
| 5,908,429 A | 6/1999 | Yoon | | 6,190,353 B1 | 2/2001 | Makower et al. |
| 5,911,737 A | 6/1999 | Lee et al. | | 6,190,384 B1 | 2/2001 | Ouchi |
| 5,916,146 A | 6/1999 | Allotta et al. | | 6,190,399 B1 | 2/2001 | Palmer et al. |
| 5,916,147 A | 6/1999 | Boury | | 6,203,533 B1 | 3/2001 | Ouchi |
| 5,921,993 A | 7/1999 | Yoon | | 6,206,872 B1 | 3/2001 | Lafond et al. |
| 5,921,997 A | 7/1999 | Fogelberg et al. | | 6,206,877 B1 | 3/2001 | Kese et al. |
| 5,922,008 A | 7/1999 | Gimpelson | | 6,214,007 B1 | 4/2001 | Anderson |
| 5,925,052 A | 7/1999 | Simmons | | 6,228,096 B1 | 5/2001 | Marchand |
| 5,928,255 A | 7/1999 | Meade et al. | | 6,234,958 B1 | 5/2001 | Snoke et al. |
| 5,928,266 A | 7/1999 | Kontos | | 6,245,079 B1 | 6/2001 | Nobles et al. |
| 5,936,536 A | 8/1999 | Morris | | 6,246,914 B1 | 6/2001 | de la Rama et al. |
| 5,944,718 A | 8/1999 | Austin et al. | | 6,258,064 B1 | 7/2001 | Smith et al. |
| 5,951,547 A | 9/1999 | Gough et al. | | 6,261,242 B1 | 7/2001 | Roberts et al. |
| 5,951,549 A | 9/1999 | Richardson et al. | | 6,264,664 B1 | 7/2001 | Avellanet |
| 5,954,720 A | 9/1999 | Wilson et al. | | 6,270,497 B1 | 8/2001 | Sekino et al. |
| 5,954,731 A | 9/1999 | Yoon | | 6,270,505 B1 | 8/2001 | Yoshida et al. |
| 5,957,943 A | 9/1999 | Vaitekunas | | 6,277,136 B1 | 8/2001 | Bonutti |
| 5,957,953 A | 9/1999 | DiPoto et al. | | 6,283,963 B1 | 9/2001 | Regula |
| 5,971,995 A | 10/1999 | Rousseau | | 6,293,909 B1 | 9/2001 | Chu et al. |
| 5,972,002 A | 10/1999 | Bark et al. | | 6,293,952 B1 | 9/2001 | Brosens et al. |
| 5,976,074 A | 11/1999 | Moriyama | | 6,296,630 B1 | 10/2001 | Altman et al. |
| 5,976,075 A | 11/1999 | Beane et al. | | 6,314,963 B1 | 11/2001 | Vaska et al. |
| 5,976,130 A | 11/1999 | McBrayer et al. | | 6,322,578 B1 | 11/2001 | Houle et al. |
| 5,976,131 A | 11/1999 | Guglielmi et al. | | 6,326,177 B1 | 12/2001 | Schoenbach et al. |
| 5,980,539 A | 11/1999 | Kontos | | 6,328,730 B1 | 12/2001 | Harkrider, Jr. |
| 5,980,556 A | 11/1999 | Giordano et al. | | 6,350,267 B1 | 2/2002 | Stefanchik |
| 5,984,938 A | 11/1999 | Yoon | | 6,350,278 B1 | 2/2002 | Lenker et al. |
| 5,984,939 A | 11/1999 | Yoon | | 6,352,503 B1 | 3/2002 | Matsui et al. |
| 5,989,182 A | 11/1999 | Hori et al. | | 6,352,543 B1 | 3/2002 | Cole |
| 5,993,447 A | 11/1999 | Blewett et al. | | 6,355,013 B1 | 3/2002 | van Muiden |
| 5,997,555 A | 12/1999 | Kontos | | 6,355,035 B1 | 3/2002 | Manushakian |
| 6,001,120 A | 12/1999 | Levin | | 6,361,534 B1 | 3/2002 | Chen et al. |
| 6,004,269 A | 12/1999 | Crowley et al. | | 6,371,956 B1 | 4/2002 | Wilson et al. |
| 6,004,330 A | 12/1999 | Middleman et al. | | 6,379,366 B1 | 4/2002 | Fleischman et al. |
| 6,007,566 A | 12/1999 | Wenstrom, Jr. | | 6,383,195 B1 | 5/2002 | Richard |
| 6,010,515 A | 1/2000 | Swain et al. | | 6,383,197 B1 | 5/2002 | Conlon et al. |
| 6,012,494 A | 1/2000 | Balazs | | 6,387,671 B1 | 5/2002 | Rubinsky et al. |
| 6,017,356 A | 1/2000 | Frederick et al. | | 6,391,029 B1 | 5/2002 | Hooven et al. |
| 6,019,770 A | 2/2000 | Christoudias | | 6,402,735 B1 | 6/2002 | Langevin |
| 6,024,708 A | 2/2000 | Bales et al. | | 6,406,440 B1 | 6/2002 | Stefanchik |
| 6,024,747 A | 2/2000 | Kontos | | 6,409,727 B1 | 6/2002 | Bales et al. |
| 6,027,522 A | 2/2000 | Palmer | | 6,409,733 B1 | 6/2002 | Conlon et al. |
| 6,030,365 A | 2/2000 | Laufer | | 6,419,641 B1 | 7/2002 | Mark et al. |
| 6,030,634 A | 2/2000 | Wu et al. | | 6,427,089 B1 | 7/2002 | Knowlton |
| 6,033,399 A | 3/2000 | Gines | | 6,431,500 B1 | 8/2002 | Jacobs et al. |
| 6,036,685 A | 3/2000 | Mueller | | 6,436,107 B1 | 8/2002 | Wang et al. |
| 6,053,927 A | 4/2000 | Hamas | | 6,443,970 B1 | 9/2002 | Schulze et al. |
| 6,066,160 A | 5/2000 | Colvin et al. | | 6,443,988 B2 | 9/2002 | Felt et al. |
| 6,068,603 A | 5/2000 | Suzuki | | 6,447,511 B1 | 9/2002 | Slater |
| 6,068,629 A | 5/2000 | Haissaguerre et al. | | 6,447,523 B1 | 9/2002 | Middleman et al. |
| 6,071,233 A | 6/2000 | Ishikawa et al. | | 6,454,783 B1 | 9/2002 | Piskun |
| 6,074,408 A | 6/2000 | Freeman | | 6,454,785 B2 | 9/2002 | De Hoyos Garza |
| 6,086,530 A | 7/2000 | Mack | | 6,458,076 B1 | 10/2002 | Pruitt |
| 6,090,105 A | 7/2000 | Zepeda et al. | | 6,464,701 B1 | 10/2002 | Hooven et al. |
| 6,090,108 A | 7/2000 | McBrayer et al. | | 6,464,702 B2 | 10/2002 | Schulze et al. |
| 6,096,046 A | 8/2000 | Weiss | | 6,470,218 B1 | 10/2002 | Behl |
| 6,102,926 A | 8/2000 | Tartaglia et al. | | 6,475,104 B1 | 11/2002 | Lutz et al. |
| 6,106,473 A | 8/2000 | Violante et al. | | 6,485,411 B1 | 11/2002 | Konstorum et al. |
| 6,109,852 A | 8/2000 | Shahinpoor et al. | | 6,489,745 B1 | 12/2002 | Koreis |
| 6,110,154 A | 8/2000 | Shimomura et al. | | 6,491,626 B1 | 12/2002 | Stone et al. |
| 6,110,183 A | 8/2000 | Cope | | 6,491,627 B1 | 12/2002 | Komi |
| 6,113,593 A | 9/2000 | Tu et al. | | 6,491,691 B1 | 12/2002 | Morley et al. |
| 6,117,144 A | 9/2000 | Nobles et al. | | 6,493,590 B1 | 12/2002 | Wessman et al. |
| 6,117,158 A | 9/2000 | Measamer et al. | | 6,494,893 B2 | 12/2002 | Dubrul et al. |
| 6,139,555 A | 10/2000 | Hart et al. | | 6,500,176 B1 | 12/2002 | Truckai et al. |
| 6,141,037 A | 10/2000 | Upton et al. | | 6,503,192 B1 | 1/2003 | Ouchi |
| 6,146,391 A | 11/2000 | Cigaina | | 6,506,190 B1 | 1/2003 | Walshe |
| 6,148,222 A | 11/2000 | Ramsey, III | | 6,508,827 B1 | 1/2003 | Manhes |
| 6,149,653 A | 11/2000 | Deslauriers | | 6,514,239 B2 | 2/2003 | Shimmura et al. |
| 6,149,662 A | 11/2000 | Pugliesi et al. | | 6,520,954 B2 | 2/2003 | Ouchi |
| 6,156,006 A | 12/2000 | Brosens et al. | | 6,527,782 B2 | 3/2003 | Hogg et al. |

| | | |
|---|---|---|
| 6,543,456 B1 | 4/2003 | Freeman |
| 6,551,270 B1 | 4/2003 | Bimbo et al. |
| 6,554,766 B2 | 4/2003 | Maeda et al. |
| 6,554,829 B2 | 4/2003 | Schulze et al. |
| 6,558,384 B2 | 5/2003 | Mayenberger |
| 6,562,035 B1 | 5/2003 | Levin |
| 6,562,052 B1 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,638,286 B1 | 10/2003 | Burbank et al. |
| 6,645,225 B1 | 11/2003 | Atkinson |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |
| 6,686,724 B2 | 2/2004 | Coates et al. |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,166 B2 | 6/2004 | Berci et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,918,908 B2 | 7/2005 | Bonner et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |

| Patent | Kind | Date | Inventor |
|---|---|---|---|
| 7,101,373 | B2 | 9/2006 | Dycus et al. |
| 7,105,000 | B2 | 9/2006 | McBrayer |
| 7,105,005 | B2 | 9/2006 | Blake |
| 7,108,696 | B2 | 9/2006 | Daniel et al. |
| 7,108,703 | B2 | 9/2006 | Danitz et al. |
| 7,112,208 | B2 | 9/2006 | Morris et al. |
| 7,115,092 | B2 | 10/2006 | Park et al. |
| 7,117,703 | B2 | 10/2006 | Kato et al. |
| 7,118,531 | B2 | 10/2006 | Krill |
| 7,118,578 | B2 | 10/2006 | West, Jr. et al. |
| 7,118,587 | B2 | 10/2006 | Dycus et al. |
| 7,128,708 | B2 | 10/2006 | Saadat et al. |
| RE39,415 | E | 11/2006 | Bales et al. |
| 7,131,978 | B2 | 11/2006 | Sancoff et al. |
| 7,131,979 | B2 | 11/2006 | DiCarlo et al. |
| 7,131,980 | B1 | 11/2006 | Field et al. |
| 7,137,980 | B2 | 11/2006 | Buysse et al. |
| 7,137,981 | B2 | 11/2006 | Long |
| 7,146,984 | B2 | 12/2006 | Stack et al. |
| 7,147,650 | B2 | 12/2006 | Lee |
| 7,150,097 | B2 | 12/2006 | Sremcich et al. |
| 7,150,655 | B2 | 12/2006 | Mastrototaro et al. |
| 7,152,488 | B2 | 12/2006 | Hedrich et al. |
| 7,153,321 | B2 | 12/2006 | Andrews |
| 7,160,296 | B2 | 1/2007 | Pearson et al. |
| 7,163,525 | B2 | 1/2007 | Franer |
| 7,172,714 | B2 | 2/2007 | Jacobson |
| 7,179,254 | B2 | 2/2007 | Pendekanti et al. |
| 7,188,627 | B2 | 3/2007 | Nelson et al. |
| 7,195,612 | B2 | 3/2007 | Van Sloten et al. |
| 7,195,631 | B2 | 3/2007 | Dumbauld |
| 7,204,820 | B2 | 4/2007 | Akahoshi |
| 7,208,005 | B2 | 4/2007 | Frecker et al. |
| 7,211,092 | B2 | 5/2007 | Hughett |
| 7,220,227 | B2 | 5/2007 | Sasaki et al. |
| 7,223,272 | B2 | 5/2007 | Francese et al. |
| 7,229,438 | B2 | 6/2007 | Young |
| 7,232,414 | B2 | 6/2007 | Gonzalez |
| 7,232,445 | B2 | 6/2007 | Kortenbach et al. |
| 7,241,290 | B2 | 7/2007 | Doyle et al. |
| 7,244,228 | B2 | 7/2007 | Lubowski |
| 7,250,027 | B2 | 7/2007 | Barry |
| 7,252,660 | B2 | 8/2007 | Kunz |
| 7,255,675 | B2 | 8/2007 | Gertner et al. |
| 7,270,663 | B2 | 9/2007 | Nakao |
| 7,294,139 | B1 | 11/2007 | Gengler |
| 7,301,250 | B2 | 11/2007 | Cassel |
| 7,306,597 | B2 | 12/2007 | Manzo |
| 7,308,828 | B2 | 12/2007 | Hashimoto |
| 7,318,802 | B2 | 1/2008 | Suzuki et al. |
| 7,320,695 | B2 | 1/2008 | Carroll |
| 7,322,934 | B2 | 1/2008 | Miyake et al. |
| 7,323,006 | B2 | 1/2008 | Andreas et al. |
| 7,329,256 | B2 | 2/2008 | Johnson et al. |
| 7,329,257 | B2 | 2/2008 | Kanehira et al. |
| 7,329,383 | B2 | 2/2008 | Stinson |
| 7,344,536 | B1 | 3/2008 | Lunsford et al. |
| 7,352,387 | B2 | 4/2008 | Yamamoto |
| 7,364,582 | B2 | 4/2008 | Lee |
| 7,371,215 | B2 | 5/2008 | Colliou et al. |
| 7,381,216 | B2 | 6/2008 | Buzzard et al. |
| 7,393,322 | B2 | 7/2008 | Wenchell |
| 7,402,162 | B2 | 7/2008 | Ouchi |
| 7,404,791 | B2 | 7/2008 | Linares et al. |
| 7,410,483 | B2 | 8/2008 | Danitz et al. |
| 7,413,563 | B2 | 8/2008 | Corcoran et al. |
| 7,416,554 | B2 | 8/2008 | Lam et al. |
| 7,422,590 | B2 | 9/2008 | Kupferschmid et al. |
| 7,435,257 | B2 | 10/2008 | Lashinski et al. |
| 7,452,327 | B2 | 11/2008 | Durgin et al. |
| 7,455,208 | B2 | 11/2008 | Wales et al. |
| 7,468,066 | B2 | 12/2008 | Vargas et al. |
| 7,488,295 | B2 | 2/2009 | Burbank et al. |
| 7,494,499 | B2 | 2/2009 | Nagase et al. |
| 7,497,867 | B2 | 3/2009 | Lasner et al. |
| 7,498,950 | B1 | 3/2009 | Ertas et al. |
| 7,507,200 | B2 | 3/2009 | Okada |
| 7,510,107 | B2 | 3/2009 | Timm et al. |
| 7,511,733 | B2 | 3/2009 | Takizawa et al. |
| 7,515,953 | B2 | 4/2009 | Madar et al. |
| 7,520,876 | B2 | 4/2009 | Ressemann et al. |
| 7,524,281 | B2 | 4/2009 | Chu et al. |
| 7,524,302 | B2 | 4/2009 | Tower |
| 7,534,228 | B2 | 5/2009 | Williams |
| 7,540,872 | B2 | 6/2009 | Schechter et al. |
| 7,544,203 | B2 | 6/2009 | Chin et al. |
| 7,548,040 | B2 | 6/2009 | Lee et al. |
| 7,549,564 | B2 | 6/2009 | Boudreaux |
| 7,553,278 | B2 | 6/2009 | Kucklick |
| 7,553,298 | B2 | 6/2009 | Hunt et al. |
| 7,559,887 | B2 | 7/2009 | Dannan |
| 7,559,916 | B2 | 7/2009 | Smith et al. |
| 7,560,006 | B2 | 7/2009 | Rakos et al. |
| 7,561,916 | B2 | 7/2009 | Hunt et al. |
| 7,566,334 | B2 | 7/2009 | Christian et al. |
| 7,575,144 | B2 | 8/2009 | Ortiz et al. |
| 7,575,548 | B2 | 8/2009 | Takemoto et al. |
| 7,579,550 | B2 | 8/2009 | Dayton et al. |
| 7,582,096 | B2 | 9/2009 | Gellman et al. |
| 7,588,177 | B2 | 9/2009 | Racenet |
| 7,588,557 | B2 | 9/2009 | Nakao |
| 7,597,229 | B2 | 10/2009 | Boudreaux et al. |
| 7,604,150 | B2 | 10/2009 | Boudreaux |
| 7,608,083 | B2 | 10/2009 | Lee et al. |
| 7,618,398 | B2 | 11/2009 | Holman et al. |
| 7,632,250 | B2 | 12/2009 | Smith et al. |
| 7,635,373 | B2 | 12/2009 | Ortiz |
| 7,637,903 | B2 | 12/2009 | Lentz et al. |
| 7,650,742 | B2 | 1/2010 | Ushijima |
| 7,651,483 | B2 | 1/2010 | Byrum et al. |
| 7,651,509 | B2 | 1/2010 | Bojarski et al. |
| 7,654,431 | B2 | 2/2010 | Hueil et al. |
| 7,662,089 | B2 | 2/2010 | Okada et al. |
| 7,666,180 | B2 | 2/2010 | Holsten et al. |
| 7,666,203 | B2 | 2/2010 | Chanduszko et al. |
| 7,674,259 | B2 | 3/2010 | Shadduck |
| 7,678,043 | B2 | 3/2010 | Gilad |
| 7,684,599 | B2 | 3/2010 | Horn et al. |
| 7,697,970 | B2 | 4/2010 | Uchiyama et al. |
| 7,699,835 | B2 | 4/2010 | Lee et al. |
| 7,713,189 | B2 | 5/2010 | Hanke |
| 7,713,270 | B2 | 5/2010 | Suzuki |
| 7,736,374 | B2 | 6/2010 | Vaughan et al. |
| 7,744,615 | B2 | 6/2010 | Couture |
| 7,753,933 | B2 | 7/2010 | Ginn et al. |
| 7,758,577 | B2 | 7/2010 | Nobis et al. |
| 7,762,949 | B2 | 7/2010 | Nakao |
| 7,762,998 | B2 | 7/2010 | Birk et al. |
| 7,763,012 | B2 | 7/2010 | Petrick et al. |
| 7,771,416 | B2 | 8/2010 | Spivey et al. |
| 7,780,683 | B2 | 8/2010 | Roue et al. |
| 7,780,691 | B2 | 8/2010 | Stefanchik |
| 7,784,663 | B2 | 8/2010 | Shelton, IV |
| 7,794,409 | B2 | 9/2010 | Damarati |
| 7,794,475 | B2 | 9/2010 | Hess et al. |
| 7,798,386 | B2 | 9/2010 | Schall et al. |
| 7,815,659 | B2 * | 10/2010 | Conlon et al. ............... 606/198 |
| 7,828,186 | B2 | 11/2010 | Wales |
| 7,837,615 | B2 | 11/2010 | Le et al. |
| 7,842,028 | B2 | 11/2010 | Lee |
| 7,842,068 | B2 | 11/2010 | Ginn |
| 7,846,171 | B2 | 12/2010 | Kullas et al. |
| 7,850,660 | B2 | 12/2010 | Uth et al. |
| 7,857,183 | B2 | 12/2010 | Shelton, IV |
| 7,862,546 | B2 | 1/2011 | Conlon et al. |
| 7,867,216 | B2 | 1/2011 | Wahr et al. |
| 7,892,220 | B2 | 2/2011 | Faller et al. |
| 7,896,887 | B2 | 3/2011 | Rimbaugh et al. |
| 7,905,828 | B2 | 3/2011 | Brock et al. |
| 7,909,809 | B2 | 3/2011 | Scopton et al. |
| 7,914,513 | B2 | 3/2011 | Voorhees, Jr. |
| 7,918,869 | B2 | 4/2011 | Saadat et al. |
| 7,931,624 | B2 | 4/2011 | Smith et al. |
| 7,945,332 | B2 | 5/2011 | Schechter |
| 7,947,000 | B2 | 5/2011 | Vargas et al. |
| 7,955,298 | B2 | 6/2011 | Carroll et al. |
| 7,963,975 | B2 | 6/2011 | Criscuolo |
| 7,965,180 | B2 | 6/2011 | Koyama |

| Patent/Publication | Date | Name |
|---|---|---|
| 7,969,473 B2 | 6/2011 | Kotoda |
| 7,988,685 B2 | 8/2011 | Ziaie et al. |
| 8,048,067 B2 | 11/2011 | Davalos et al. |
| 8,057,510 B2 | 11/2011 | Ginn et al. |
| 8,066,632 B2 | 11/2011 | Dario et al. |
| 8,075,587 B2 | 12/2011 | Ginn |
| 8,088,062 B2 | 1/2012 | Zwolinski |
| 8,118,821 B2 | 2/2012 | Mouw |
| 8,147,424 B2 | 4/2012 | Kassab et al. |
| 2001/0023333 A1 | 9/2001 | Wise et al. |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |

| | | | | | |
|---|---|---|---|---|---|
| 2005/0277956 A1 | 12/2005 | Francese et al. | 2006/0264904 A1 | 11/2006 | Kerby et al. |
| 2005/0277957 A1 | 12/2005 | Kuhns et al. | 2006/0264930 A1 | 11/2006 | Nishimura |
| 2005/0283118 A1 | 12/2005 | Uth et al. | 2006/0270902 A1 | 11/2006 | Igarashi et al. |
| 2005/0283119 A1 | 12/2005 | Uth et al. | 2006/0271042 A1 | 11/2006 | Latterell et al. |
| 2005/0288555 A1 | 12/2005 | Binmoeller | 2006/0271102 A1 | 11/2006 | Bosshard et al. |
| 2006/0004406 A1 | 1/2006 | Wehrstein et al. | 2006/0276835 A1 | 12/2006 | Uchida |
| 2006/0004409 A1 | 1/2006 | Nobis et al. | 2006/0281970 A1 | 12/2006 | Stokes et al. |
| 2006/0004410 A1 | 1/2006 | Nobis et al. | 2006/0282106 A1 | 12/2006 | Cole et al. |
| 2006/0015009 A1 | 1/2006 | Jaffe et al. | 2006/0285732 A1 | 12/2006 | Horn et al. |
| 2006/0020167 A1 | 1/2006 | Sitzmann | 2006/0287644 A1 | 12/2006 | Inganas et al. |
| 2006/0020247 A1 | 1/2006 | Kagan et al. | 2006/0287666 A1 | 12/2006 | Saadat et al. |
| 2006/0025654 A1 | 2/2006 | Suzuki et al. | 2006/0293626 A1 | 12/2006 | Byrum et al. |
| 2006/0025781 A1 | 2/2006 | Young et al. | 2007/0002135 A1 | 1/2007 | Glukhovsky |
| 2006/0025812 A1 | 2/2006 | Shelton, IV | 2007/0005019 A1 | 1/2007 | Okishige |
| 2006/0025819 A1 | 2/2006 | Nobis et al. | 2007/0010801 A1 | 1/2007 | Chen et al. |
| 2006/0036267 A1 | 2/2006 | Saadat et al. | 2007/0015965 A1 | 1/2007 | Cox et al. |
| 2006/0041188 A1 | 2/2006 | Dirusso et al. | 2007/0016225 A1 | 1/2007 | Nakao |
| 2006/0058582 A1 | 3/2006 | Maahs et al. | 2007/0032700 A1 | 2/2007 | Fowler et al. |
| 2006/0058776 A1 | 3/2006 | Bilsbury | 2007/0032701 A1 | 2/2007 | Fowler et al. |
| 2006/0069396 A1 | 3/2006 | Meade et al. | 2007/0043261 A1 | 2/2007 | Watanabe et al. |
| 2006/0069424 A1 | 3/2006 | Acosta et al. | 2007/0043345 A1 | 2/2007 | Davalos et al. |
| 2006/0069425 A1 | 3/2006 | Hillis et al. | 2007/0049800 A1 | 3/2007 | Boulais |
| 2006/0069429 A1 | 3/2006 | Spence et al. | 2007/0049902 A1 | 3/2007 | Griffin et al. |
| 2006/0074413 A1 | 4/2006 | Behzadian | 2007/0051375 A1 | 3/2007 | Milliman |
| 2006/0079890 A1 | 4/2006 | Guerra | 2007/0060880 A1 | 3/2007 | Gregorich et al. |
| 2006/0089528 A1 | 4/2006 | Tartaglia et al. | 2007/0067017 A1 | 3/2007 | Trapp |
| 2006/0095031 A1 | 5/2006 | Ormsby | 2007/0073102 A1 | 3/2007 | Matsuno et al. |
| 2006/0095060 A1 | 5/2006 | Mayenberger et al. | 2007/0073269 A1 | 3/2007 | Becker |
| 2006/0100687 A1 | 5/2006 | Fahey et al. | 2007/0079924 A1 | 4/2007 | Saadat et al. |
| 2006/0106423 A1 | 5/2006 | Weisel et al. | 2007/0088370 A1 | 4/2007 | Kahle et al. |
| 2006/0111209 A1 | 5/2006 | Hinman et al. | 2007/0100375 A1 | 5/2007 | Mikkaichi et al. |
| 2006/0111210 A1 | 5/2006 | Hinman et al. | 2007/0100376 A1 | 5/2007 | Mikkaichi et al. |
| 2006/0111704 A1 | 5/2006 | Brenneman et al. | 2007/0106118 A1 | 5/2007 | Moriyama |
| 2006/0129166 A1 | 6/2006 | Lavelle | 2007/0112251 A1 | 5/2007 | Nakhuda |
| 2006/0135962 A1 | 6/2006 | Kick et al. | 2007/0112331 A1 | 5/2007 | Weber et al. |
| 2006/0135971 A1 | 6/2006 | Swanstrom et al. | 2007/0112342 A1 | 5/2007 | Pearson et al. |
| 2006/0135984 A1 | 6/2006 | Kramer et al. | 2007/0112383 A1 | 5/2007 | Conlon et al. |
| 2006/0142644 A1 | 6/2006 | Mulac et al. | 2007/0112384 A1 | 5/2007 | Conlon et al. |
| 2006/0142652 A1 | 6/2006 | Keenan | 2007/0112385 A1 | 5/2007 | Conlon |
| 2006/0142790 A1 | 6/2006 | Gertner | 2007/0112417 A1 | 5/2007 | Shanley et al. |
| 2006/0142798 A1 | 6/2006 | Holman et al. | 2007/0112425 A1 | 5/2007 | Schaller et al. |
| 2006/0149131 A1 | 7/2006 | Or | 2007/0118115 A1 | 5/2007 | Artale et al. |
| 2006/0149132 A1 | 7/2006 | Iddan | 2007/0123840 A1 | 5/2007 | Cox |
| 2006/0149135 A1 | 7/2006 | Paz | 2007/0129605 A1 | 6/2007 | Schaaf |
| 2006/0161190 A1 | 7/2006 | Gadberry et al. | 2007/0129719 A1 | 6/2007 | Kendale et al. |
| 2006/0167416 A1 | 7/2006 | Mathis et al. | 2007/0129760 A1 | 6/2007 | Demarais et al. |
| 2006/0167482 A1 | 7/2006 | Swain et al. | 2007/0135709 A1 | 6/2007 | Rioux et al. |
| 2006/0178560 A1 | 8/2006 | Saadat et al. | 2007/0135803 A1 | 6/2007 | Belson |
| 2006/0183975 A1 | 8/2006 | Saadat et al. | 2007/0142706 A1 | 6/2007 | Matsui et al. |
| 2006/0184161 A1 | 8/2006 | Maahs et al. | 2007/0142780 A1 | 6/2007 | Van Lue |
| 2006/0189844 A1 | 8/2006 | Tien | 2007/0154460 A1 | 7/2007 | Kraft et al. |
| 2006/0189845 A1 | 8/2006 | Maahs et al. | 2007/0156028 A1 | 7/2007 | Van Lue et al. |
| 2006/0190027 A1 | 8/2006 | Downey | 2007/0156127 A1 | 7/2007 | Rioux et al. |
| 2006/0195084 A1 | 8/2006 | Slater | 2007/0161855 A1 | 7/2007 | Mikkaichi et al. |
| 2006/0200005 A1 | 9/2006 | Bjork et al. | 2007/0162101 A1 | 7/2007 | Burgermeister et al. |
| 2006/0200121 A1 | 9/2006 | Mowery | 2007/0167901 A1 | 7/2007 | Herrig et al. |
| 2006/0200169 A1 | 9/2006 | Sniffin | 2007/0173691 A1 | 7/2007 | Yokoi et al. |
| 2006/0200170 A1 | 9/2006 | Aranyi | 2007/0173869 A1 | 7/2007 | Gannoe et al. |
| 2006/0200199 A1 | 9/2006 | Bonutti et al. | 2007/0173870 A2 | 7/2007 | Zacharias |
| 2006/0217665 A1 | 9/2006 | Prosek | 2007/0173872 A1 | 7/2007 | Neuenfeldt |
| 2006/0217697 A1 | 9/2006 | Lau et al. | 2007/0179525 A1 | 8/2007 | Frecker et al. |
| 2006/0217742 A1 | 9/2006 | Messerly et al. | 2007/0179530 A1 | 8/2007 | Tieu et al. |
| 2006/0217743 A1 | 9/2006 | Messerly et al. | 2007/0197865 A1 | 8/2007 | Miyake et al. |
| 2006/0229639 A1 | 10/2006 | Whitfield | 2007/0198057 A1 | 8/2007 | Gelbart et al. |
| 2006/0229640 A1 | 10/2006 | Whitfield | 2007/0203487 A1 | 8/2007 | Sugita |
| 2006/0237022 A1 | 10/2006 | Chen et al. | 2007/0208336 A1 | 9/2007 | Kim et al. |
| 2006/0237023 A1 | 10/2006 | Cox et al. | 2007/0208364 A1 | 9/2007 | Smith et al. |
| 2006/0241570 A1 | 10/2006 | Wilk | 2007/0213754 A1 | 9/2007 | Mikkaichi et al. |
| 2006/0247576 A1 | 11/2006 | Poncet | 2007/0225554 A1 | 9/2007 | Maseda et al. |
| 2006/0247673 A1 | 11/2006 | Voegele et al. | 2007/0233040 A1 | 10/2007 | Macnamara et al. |
| 2006/0253004 A1 | 11/2006 | Frisch et al. | 2007/0244358 A1 | 10/2007 | Lee |
| 2006/0253039 A1 | 11/2006 | McKenna et al. | 2007/0250038 A1 | 10/2007 | Boulais |
| 2006/0258907 A1 | 11/2006 | Stefanchik et al. | 2007/0250057 A1 | 10/2007 | Nobis et al. |
| 2006/0258908 A1 | 11/2006 | Stefanchik et al. | 2007/0255096 A1 | 11/2007 | Stefanchik et al. |
| 2006/0258910 A1 | 11/2006 | Stefanchik et al. | 2007/0255100 A1 | 11/2007 | Barlow et al. |
| 2006/0258954 A1 | 11/2006 | Timberlake et al. | 2007/0255273 A1 | 11/2007 | Fernandez et al. |
| 2006/0258955 A1 | 11/2006 | Hoffman et al. | 2007/0255303 A1 | 11/2007 | Bakos et al. |
| 2006/0259010 A1 | 11/2006 | Stefanchik et al. | 2007/0255306 A1 | 11/2007 | Conlon et al. |
| 2006/0264752 A1 | 11/2006 | Rubinsky et al. | 2007/0260112 A1 | 11/2007 | Rahmani |

| Pub. No. | Date | Inventor |
|---|---|---|
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140071 A1 | 6/2008 | Vegesna |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262513 A1 | 10/2008 | Stahler et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0216248 A1 | 8/2009 | Uenohara et al. |
| 2009/0227828 A1 | 9/2009 | Swain et al. |
| 2009/0248055 A1 | 10/2009 | Spivey et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326332 A1 | 12/2009 | Carter |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0056864 A1 | 3/2010 | Lee |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |

| | | | |
|---|---|---|---|
| 2010/0249700 A1 | 9/2010 | Spivey | |
| 2010/0261994 A1 | 10/2010 | Davalos et al. | |
| 2010/0286791 A1 | 11/2010 | Goldsmith | |
| 2010/0298642 A1 | 11/2010 | Trusty et al. | |
| 2010/0312056 A1 | 12/2010 | Galperin et al. | |
| 2010/0331622 A2 | 12/2010 | Contort | |
| 2010/0331758 A1 | 12/2010 | Davalos et al. | |
| 2010/0331774 A2 | 12/2010 | Splvey | |
| 2011/0093009 A1 | 4/2011 | Fox | |
| 2011/0098694 A1 | 4/2011 | Long | |
| 2011/0098704 A1 | 4/2011 | Long et al. | |
| 2011/0105850 A1 | 5/2011 | Voegele et al. | |
| 2011/0106221 A1 | 5/2011 | Neal, II et al. | |
| 2011/0112434 A1 | 5/2011 | Ghabrial et al. | |
| 2011/0115891 A1 | 5/2011 | Trusty | |
| 2011/0124964 A1 | 5/2011 | Nobis | |
| 2011/0152609 A1 | 6/2011 | Trusty et al. | |
| 2011/0152610 A1 | 6/2011 | Trusty et al. | |
| 2011/0152612 A1 | 6/2011 | Trusty et al. | |
| 2011/0152858 A1 | 6/2011 | Long et al. | |
| 2011/0152859 A1 | 6/2011 | Long et al. | |
| 2011/0152878 A1 | 6/2011 | Trusty et al. | |
| 2011/0152923 A1 | 6/2011 | Fox | |
| 2011/0160514 A1 | 6/2011 | Long et al. | |
| 2011/0190659 A1 | 8/2011 | Long et al. | |
| 2011/0190764 A1 | 8/2011 | Long et al. | |
| 2011/0193948 A1 | 8/2011 | Amling et al. | |
| 2011/0245619 A1 | 10/2011 | Holcomb | |
| 2011/0285488 A1 | 11/2011 | Scott et al. | |
| 2011/0306212 A1 | 12/2011 | Long | |
| 2012/0004502 A1 | 1/2012 | Weitzner et al. | |
| 2012/0088965 A1 | 4/2012 | Stokes et al. | |
| 2012/0089089 A1 | 4/2012 | Swain et al. | |
| 2012/0089093 A1 | 4/2012 | Trusty | |
| 2012/0116155 A1 | 5/2012 | Trusty | |
| 2012/0179148 A1 | 7/2012 | Conlon | |
| 2012/0191075 A1 | 7/2012 | Trusty | |
| 2012/0191076 A1 | 7/2012 | Voegele et al. | |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 1493397 B1 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2006297005 A | 11/2006 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/26708 A1 | 4/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A1 | 4/2004 |
| WO | WO 2004/037123 A1 | 5/2004 |
| WO | WO 2004/037149 A1 | 5/2004 |
| WO | WO 01/41627 A2 | 6/2004 |
| WO | WO 2004/052221 A1 | 6/2004 |
| WO | WO 2004/048827 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/065284 A2 | 7/2005 |
| WO | WO 2005/097019 A2 | 10/2005 |
| WO | WO 2005/097234 A2 | 10/2005 |

| | | |
|---|---|---|
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |

OTHER PUBLICATIONS

International Preliminary Report on Patentability for PCT/US2009/047599, mailed Jan. 13, 2011 (10 pages).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
Michael S. Kavic, M.D., "Natural Orifice Translumenal Endoscopic Surgery: "Notes"", JSLS, vol. 10, pp. 133-134 (2006).
Ethicon, Inc., "Wound Closure Manual: Chapter 3 (The Surgical Needle)," 15 pages; (publication date unknown).
Guido M. Sclabas, M.D., et al., "Endoluminal Methods for Gastrotomy Closure in Natural Orifice TransEnteric Surgery (Notes)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastroint Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey Notes Presentation to EES Notes Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37; pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
U.S. Appl. No. 11/706,591, filed Feb. 15, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.

U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
International Search Report for PCT/US2009/047599, Sep. 9, 2009 (7 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRelId=1000.1003&method=D . . . , accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for Notes," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential of Pure Notes Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal Notes Sleeve Gastrectomy in a Porcine Model Using a Magnetically Anchored Camera and Novel Instrumentation," Abstract submitted along with Poster at Sages Annual Meeting in Phoenix, AZ, Apr. 22, 2009 (1 page).
Castellvi et al., "Hybrid Transvaginal Notes Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818, filed Mar. 15, 2012.

* cited by examiner

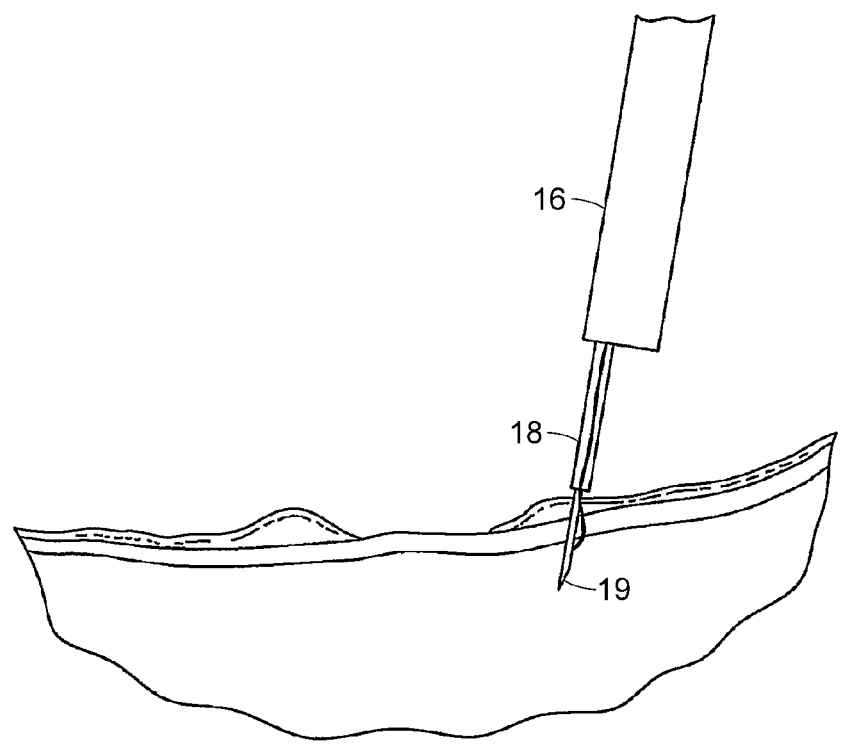
FIG. 2    (PRIOR ART)
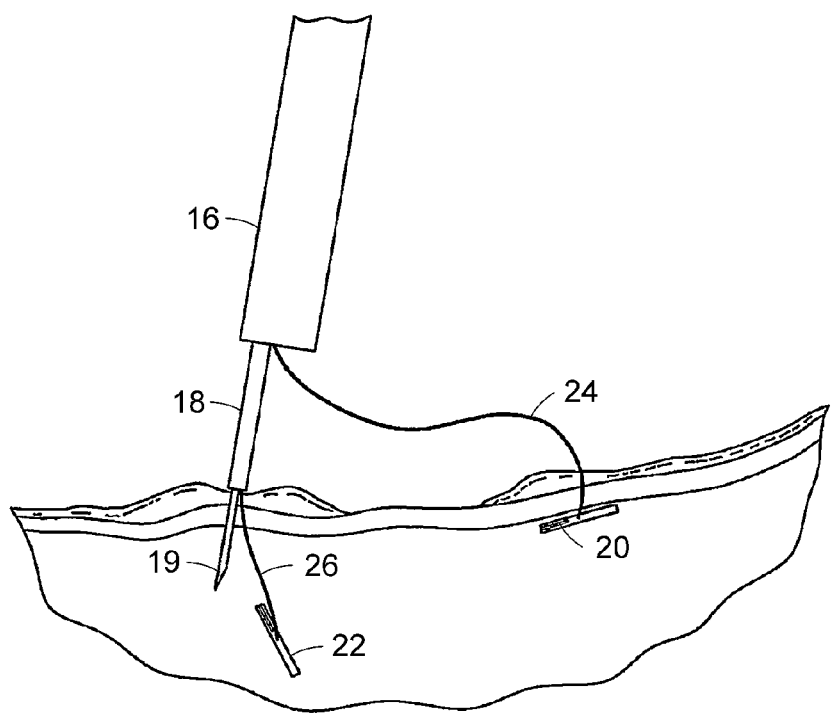
FIG. 3    (PRIOR ART)

SURGICAL SUTURE ARRANGEMENT

BACKGROUND

The present application relates to surgical fasteners and instruments for approximating and fastening tissue and, more particularly, to suture anchors and associated instruments for endoscopically attaching sutures to tissue.

Access to the abdominal cavity may, from time to time, be required for diagnostic and therapeutic endeavors for a variety of medical and surgical diseases. Historically, abdominal access has required a formal laparotomy to provide adequate exposure. Such procedures, which require incisions to be made in the abdomen, are not particularly well-suited for patients that may have extensive abdominal scarring from previous procedures, those persons who are morbidly obese, those individuals with abdominal wall infection, and those patients with diminished abdominal wall integrity, such as patients with burns and skin grafting. Other patients simply do not want to have a scar if it can be avoided.

Minimally invasive procedures are desirable because such procedures can reduce pain and provide relatively quick recovery times as compared with conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall. The trocar must pass through several layers of overlapping tissue/muscle before reaching the abdominal cavity.

Still less invasive treatments include those that are performed through insertion of an endoscope through a natural body orifice to a treatment region. Examples of this approach include, but are not limited to, cholecystectomy, appendectomy, cystoscopy, hysteroscopy, esophagogastroduodenoscopy, and colonoscopy. Many of these procedures employ the use of a flexible endoscope during the procedure. Flexible endoscopes often have a flexible, steerable articulating section near the distal end that can be controlled by the user by utilizing controls at the proximal end. Minimally invasive therapeutic procedures to treat diseased tissue by introducing medical instruments to a tissue treatment region through a natural opening of the patient are known as Natural Orifice Translumenal Endoscopic Surgery (NOTES)™.

These minimally invasive surgical procedures have changed some of the major open surgical procedures such as gall bladder removal, or a cholecystectomy, to simple outpatient surgery. Consequently, the patient's recovery time has changed from weeks to days. These types of surgeries are often used for repairing defects or for the removal of diseased tissue or organs from areas of the body such as the abdominal cavity.

The working channel of a flexible endoscope typically has a diameter in the range of about 2.5 to about 4 millimeters. Current staplers and suturing devices cannot be easily redesigned to work through such small openings. In addition, performing procedures by way of the working channel does not easily permit using two instruments positioned at different angles with respect to the wound site in order to "pass and catch" a needle and apply sutures.

Various clips, suture fasteners and anchors have been developed such that physicians (e.g., gastroenterologists) may endoscopically close perforations in the gastrointestinal tract resulting from, for example, ulcers or polypectomy. One type of suture anchor is known as a "T-tag" fastener. The T-tag is a small metallic pin with a suture attached at the middle. The physician may load the T-tag into the end of a cannulated needle of an applicator that may be inserted through the working channel of a flexible endoscope. The physician may push the needle into the tissue near the perforation and implant the T-tag into the tissue with the attached suture trailing through the working channel and out the proximal end of the endoscope. After two or more T-tags are attached to the tissue near the wound in this manner, the physician may pull the sutures to appose the tissue around the wound. The physician may then fasten the sutures together by applying a plurality of alternating, right and left overhand knots using a knot pushing device or by applying a knotting element or other type of fastener through the working channel of the endoscope.

An issue typically associated with current suture anchor applicators is the risk that nearby organs may be accidentally injured by the needle of the applicator. The physician normally cannot see anatomical structures on the distal side of the tissue layers when the needle is being pushed through the tissue layers. Therefore, there is a risk that adjacent organs may be accidentally injured by the penetrating needle.

There is a need for an improved suture anchor applicator that helps to prevent accidental injury to nearby anatomical structures during deployment of the anchor into tissue near a wound site.

The foregoing discussion is intended only to illustrate some of the shortcomings present in the field of the invention at the time, and should not be taken as a disavowal of claim scope.

FIGURES

The novel features of the various embodiments are set forth with particularity in the appended claims. The various embodiments, however, both as to organization and methods of operation, may best be understood by reference to the following description, taken in conjunction with the accompanying drawings as follows.

FIG. 2 is a drawing of the distal portion of a suture anchor applicator extending from the distal end of the gastroscope while a first suture anchor is deployed into the stomach wall near a wound.

FIG. 3 is a drawing of the applicator of FIG. 2 while a second suture anchor is deployed into the stomach wall on the opposing side of the wound.

DESCRIPTION

Before explaining the various embodiments in detail, it should be noted that the embodiments are not limited in their application or use to the details of construction and arrangement of parts illustrated in the accompanying drawings and description. The illustrative embodiments may be implemented or incorporated in other embodiments, variations and modifications, and may be practiced or carried out in various ways. For example, the suture anchor applicators and the suture anchor configurations disclosed below are illustrative only and not meant to limit the scope or application thereof. Furthermore, unless otherwise indicated, the terms and expressions employed herein have been chosen for the purpose of describing the illustrative embodiments for the convenience of the reader and are not to limit the scope thereof.

Figure 1:
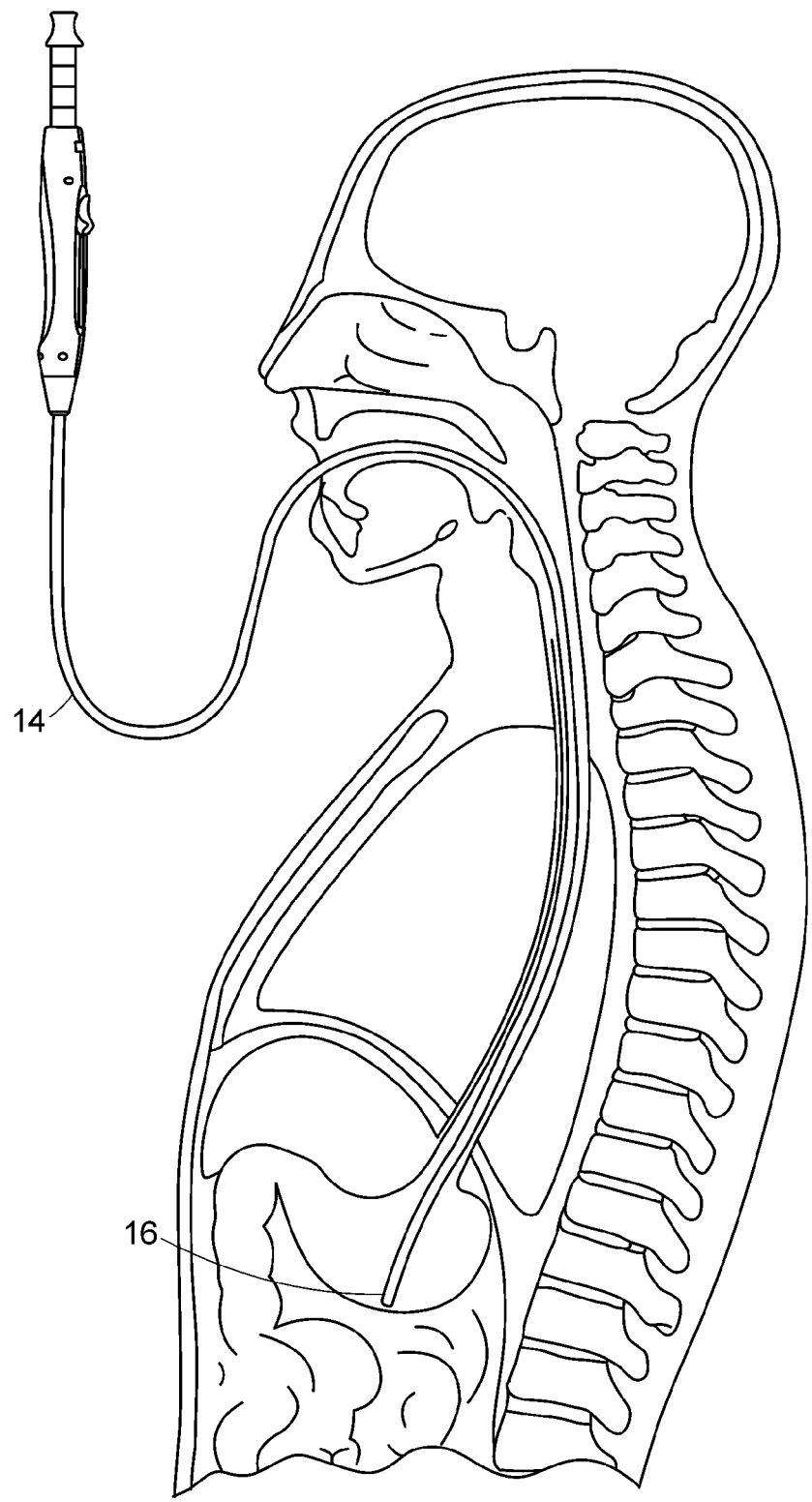
FIG. 1 is a drawing of a flexible, endoscopic portion of a gastroscope inserted into the upper gastrointestinal tract of a patient.

FIG. 1 illustrates a flexible endoscopic portion 16 of a gastroscope 14 inserted into the upper gastrointestinal tract of a patient. FIGS. 2, 3, 4 and 5 illustrate a procedure for repairing a wound such as a gastric bleeding ulcer in the stomach wall of the patient via the working channel of gastroscope 14. FIG. 2 is a drawing of the distal portion of a suture anchor applicator extending from the distal end of the gastroscope while a first suture anchor is deployed into the stomach wall near a wound. FIG. 3 is a drawing of the applicator of FIG. 2 while a second suture anchor is deployed into the stomach wall on the opposing side of the wound. As shown in FIG. 2, the physician (e.g., gastroenterologist) inserts a suture anchor applicator 18 through gastroscope 14 and penetrates a cannulated needle 19 through the stomach wall near the diseased area or wound. Needle 19 contains at least one suture anchor such that, as shown in FIG. 3, the physician may deploy a first suture anchor 20 attached to a first suture 24 to one side of the wound and a second suture anchor 22 attached to a second suture 26 to the opposite side of the wound. First and second suture anchors 20, 22 may be conventional "T-tag" fasteners or any of the suture anchor embodiments described herein or their equivalents.

Figure 4:
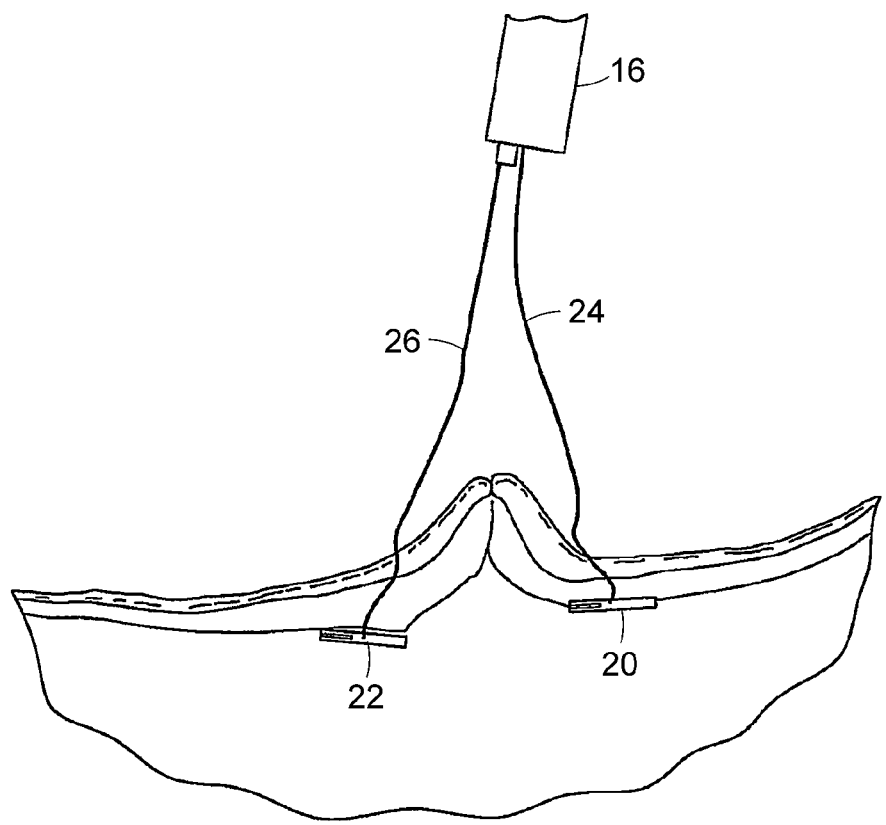
FIG. 4 is a drawing of the applicator of FIG. 2 while a pair of sutures of the first and second suture anchors are drawn together to appose the tissue on each side of the wound.
Figure 5:
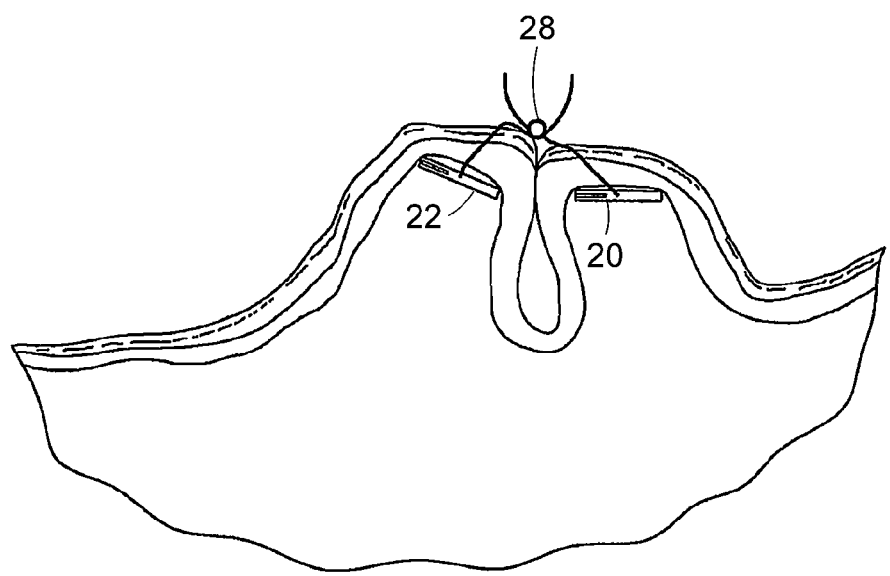
FIG. 5 is a drawing of the pair of sutures of FIG. 4 fastened together with a knotting element, thereby holding the tissue in apposition.

FIG. 4 is a drawing of the applicator of FIG. 2 while a pair of sutures of the first and second suture anchors are drawn together to appose the tissue on each side of the wound. FIG. 5 is a drawing of the pair of sutures of FIG. 4 fastened together with a knotting element, thereby holding the tissue in apposition. The free ends of first and second sutures 24, 26 may extend through the proximal end of gastroscope 14 such that, as shown in FIG. 4, the physician may draw the first and second sutures 24, 26 together to appose the tissue around the wound. The physician may then fasten the first and second sutures 24, 26 together by, for example, applying a plurality of alternating, right and left overhand knots using a knot pushing device (not shown) or by applying a knotting element 28 or other type of fastener, as shown in FIG. 5, by way of the working channel of gastroscope 14. Excess suture may be trimmed near the knot using an endoscopic cutting instrument.

When using T-tag fasteners with the technique shown in FIGS. 2-5, there are necessary conditions for the T-tag fasteners to become securely attached to the tissue. For example, it is important that the T-tag fastener reorient with respect to the suture as previously described such that the T-tag may not be easily pulled through the tissue. If the T-tag is positioned within the tissue rather than completely through the tissue into a body cavity, the T-tag still must reorient to some degree such that the suture is securely attached to the tissue.

Although the size of the cannulated needle 19 shown in FIG. 2 may vary, it may have an inner diameter of less than one millimeter. Consequently, suture anchor 22 must be very small to be loaded inside of needle 19, yet once deployed into tissue, must be sufficiently broad to resist pull-out from tissue such that considerable tension may be applied to the sutures to draw together the tissue. Therefore, it may be desirable for suture anchor 22 to expand once deployed from the applicator and/or to include features to help secure anchor 22 to the tissue. In addition, it may be desirable for suture anchor 22 to remain securely in the loaded position within applicator 18 prior to deployment into tissue to avoid the time-consuming steps of withdrawing, reloading and reinserting the applicator.

Recently, a number of medical devices have been developed that provide an auxiliary passageway along the outside of the endoscope. One example of a medical apparatus that provides an auxiliary endoscopic passageway may be found in U.S. patent application Ser. No. 10/440,957 (published as U.S. Patent Pub. No. 2004/0230095), filed May 12, 2003, and assigned to Ethicon Endo-Surgery, Inc. The auxiliary passageway may be used, perhaps in combination with the working channel of the endoscope, for several purposes, such as to insert a suture anchor applicator for access to an internal wound site. It should be understood, therefore, that descriptions herein referring to the working channel of the endoscope also include using such an auxiliary passageway.

A physician may fully penetrate the needle of a suture anchor applicator through tissue layers of an organ in order to deploy the suture anchor on the distal side of the tissue layers. The physician normally cannot see anatomical structures on the distal side of the tissue layers through the endoscope and therefore may accidentally injure nearby organs with the penetrating needle. An aspect of a suture anchor applicator, a veress-type needle configuration, is provided to help prevent such accidental injury.

Newer procedures have developed which may even be less invasive than the laparoscopic procedures used in earlier surgical procedures. Many of these procedures employ the use of a flexible endoscope during the procedure. Flexible endoscopes often have a flexible, steerable articulating section near the distal end that can be controlled by the user by utilizing controls at the proximal end. Minimally invasive therapeutic procedures to treat diseased tissue by introducing medical instruments to a tissue treatment region through a natural opening of the patient are known as Natural Orifice Translumenal Endoscopic Surgery (NOTES)™. NOTES™ is a surgical technique whereby operations can be performed trans-orally (as depicted in FIG. 1), trans-anally, and/or trans-vaginally.

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of other embodiments. Such modifications and variations are intended to be included within the scope of the claims.

It will be appreciated that the terms "proximal" and "distal" are used herein with reference to a clinician gripping the surgical instrument. Thus, the suture anchor applicators are distal with respect to the handle assemblies of the surgical instrument. It will be further appreciated that, for convenience and clarity, spatial terms such as "top" and "bottom" also are used herein with respect to the clinician gripping the handle. However, surgical instruments are used in many orientations and positions, and these terms are not intended to be limiting and absolute.

Figure 6A:
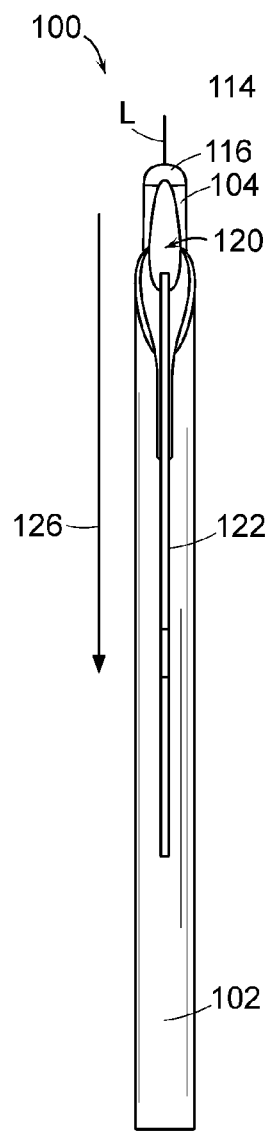
FIG. 6A is a front view of one embodiment of a suture anchor applicator.
Figure 6B:
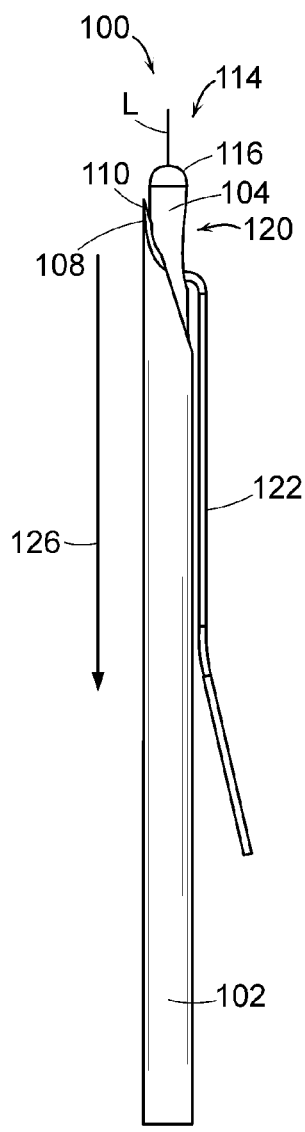
FIG. 6B is a side view of the suture anchor applicator of FIG. 6A.
Figure 6C:
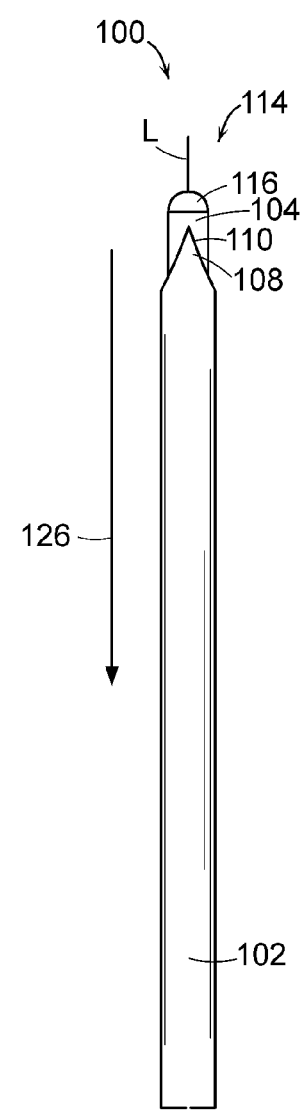
FIG. 6C is a rear view of the suture anchor applicator of FIG. 6A.

FIG. 6A is a front view of one embodiment of a suture anchor applicator 100. FIG. 6B is a side view of the suture anchor applicator 100. FIG. 6C is a rear view of the suture anchor applicator 100. As shown in FIGS. 6A-6C, the suture anchor applicator 100 may comprise a needle portion 102 and a blunt tip portion 104. The suture anchor applicator 100 is shown in FIGS. 6A-6C in a shielding, or non-compressed, position with the blunt tip portion 102 extending distally past the needle portion 104. This may allow the blunt tip portion 104 to contact tissue prior to the needle portion 102 contacting the same tissue. In operation, the suture anchor applicator 100 may be pressed against a portion of tissue such that the blunt tip portion 104 contacts the tissue. As the force applied to the suture anchor applicator 100 by the tissue is increased, the blunt tip portion 104 may slidably retract into the needle portion 102, as shown by arrow 126, until the needle portion 102 punctures the tissue and removes the force placed on the suture anchor applicator 100. Once the needle portion 102 has punctured the tissue, the blunt tip portion 104 may return to the shielding position where the blunt tip portion 104 extends past the needle portion 102.

In various embodiments, the needle portion 102 may be formed of a tube which may have a channel extending from a proximal end 106 of the needle portion 102 to a distal end 108 of the needle portion 102. The distal end 108 of the needle portion 102 may comprise a tissue penetrating tip 110. The needle portion 102 may be ground to form the tissue penetrating tip 110. The needle portion 102 may be fabricated from stainless steel hypodermic tubing or any other suitable material which may include metal and/or plastic. Alternatively, the needle portion 102 may be formed from an alternate type of metallic or polymeric tube and attached to a cannulated needle (not shown), such as by bolting, screwing, welding, crimping, gluing or any other suitable method. The needle portion 102 may have a diameter in the range of 10-35 gage. For example, the needle portion 102 may be formed from 19 gage stainless steel hypodermic tubing having an outer diameter of approximately 0.043 inches (1.09 millimeters) and a wall thickness of approximately 0.003 inches (0.076 millimeters). At least a portion of the needle portion 102 may be configured to slidably retain the blunt tip portion 104.

In various embodiments, the blunt tip portion 104 may be formed of a tube which may have a channel extending from a proximal end 112 of the blunt tip portion 104 (see FIG. 8A) to a distal end 114 of the blunt tip portion 104. The distal end 114 of the blunt tip portion 104 may comprise a blunt tip 116. The channel of the blunt tip portion 104 may be configured to retain at least one suture anchor 118 (see FIG. 9A). The blunt tip portion 104 may include an exit port 120 which may adapted for ejecting the at least one suture anchor 118. A suture 122 may be connected to the suture anchor 118 and may exit the exit port 120 proximally towards a proximal handle of a surgical device, for example, the gastroscope of FIG. 1. The blunt tip portion 104 may be fabricated from metal, plastic, or any other suitable material for such applications.

Figure 7A:
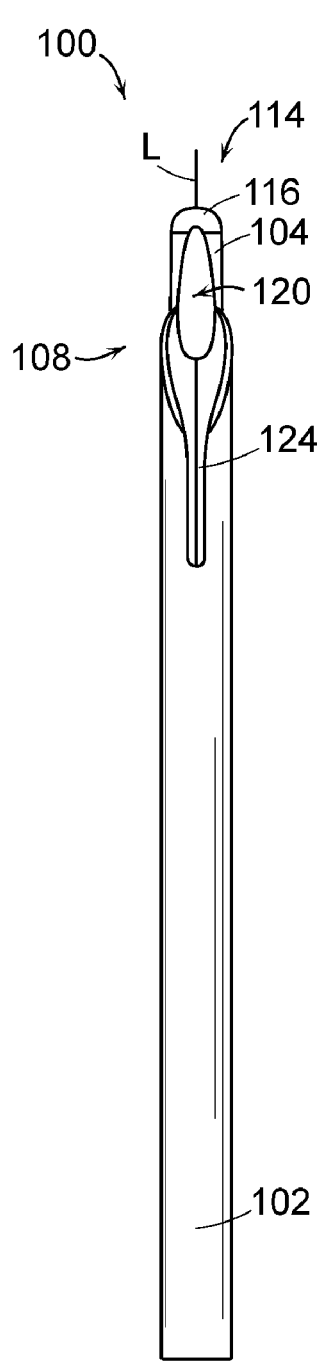
FIG. 7A is a front view of the suture anchor applicator of FIG. 6A with a suture removed.
Figure 7B:
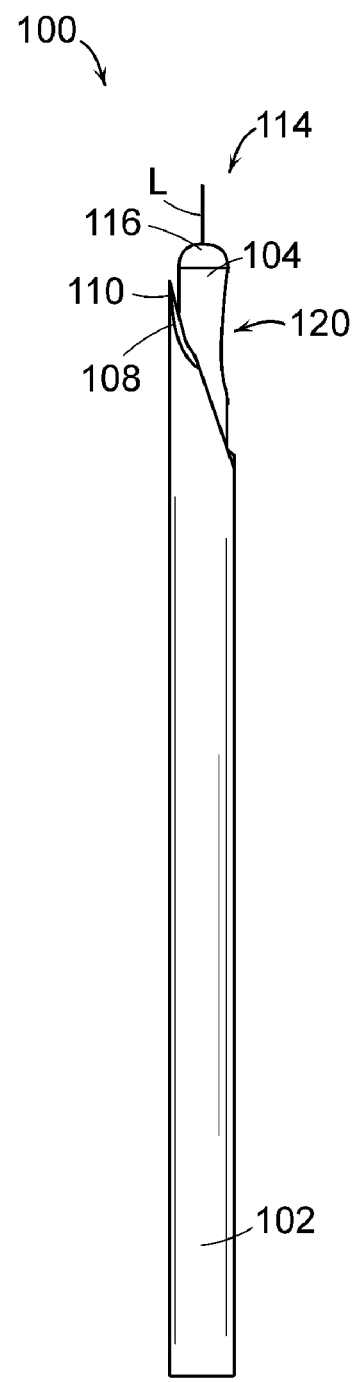
FIG. 7B is a side view of the suture anchor applicator of FIG. 6B with the suture removed.

FIG. 7A is a front view of the suture anchor applicator 100 with the suture 122 removed. FIG. 7B is a side view of the suture anchor applicator 100 with the suture 122 removed. As shown in FIG. 7A, the needle portion 102 may contain a slot 124 near the distal end 108 of the needle portion 102. The slot 124 may be configured to allow a suture 122 to run from the exit port 120 of the blunt tip portion 104 towards the proximal end of the surgical instrument. This configuration may prevent the suture 122 from being cut when the blunt tip portion 104 is slidably retracted into the needle portion 102. As discussed above, the blunt tip portion 104 may be slidably retracted into the needle portion 102 during a suture anchor placement procedure. The exit port 120 may be located on one side of the blunt tip portion 104 and may be centered along an axis "L." The slot 124 may be located on one side of the needle portion 102 and may also be centered along the axis L. The centers of the exit port 120 and the slot 124 may be substantially aligned along axis L. The suture 122 may exit the exit port 120 on the proximal end 128 of the exit port 120 and may be at least partially contained within the slot 124 during the blunt tip portion's 104 retraction.

Figure 8A:
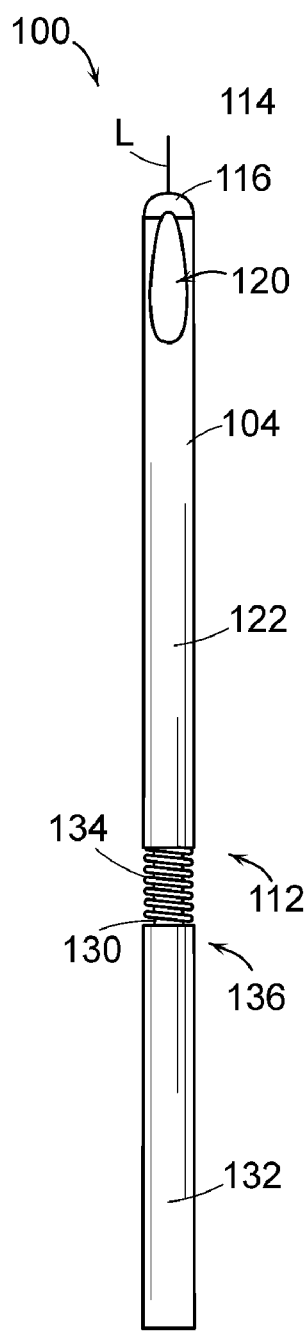
FIG. 8A is a front view of the suture anchor applicator of FIG. 7A with a needle portion removed.
Figure 8B:
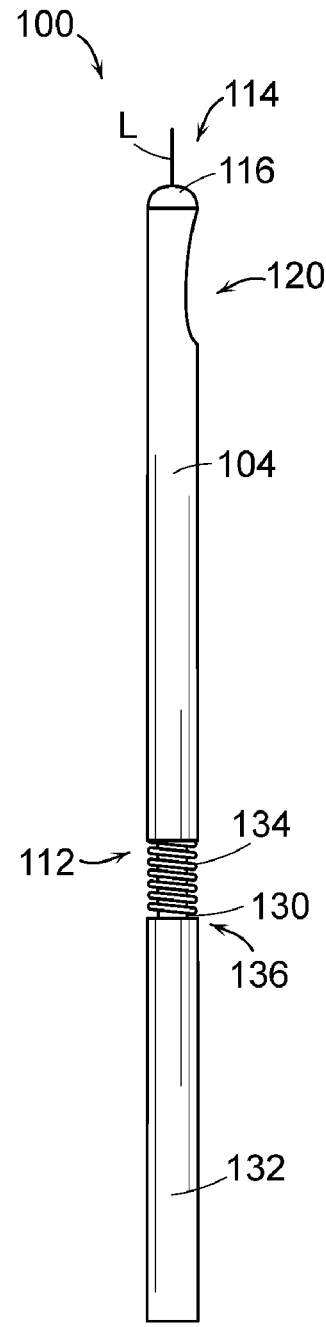
FIG. 8B is a side view of the suture anchor applicator of FIG. 7B with the needle portion removed.

FIG. 8A is a front view of the suture anchor applicator 100 with the needle portion 102 removed. FIG. 8B is a side view of the suture anchor applicator 100 with the needle portion 102 removed. As shown in FIGS. 8A-8B, the blunt tip portion 104 may be at least partially retained on a tag pusher 130. The tag pusher 130 may extend from a distal end 136 of a stylet pusher 132 through at least a portion of the channel of the blunt tip portion 104. The tag pusher 130 may be fabricated to have a cross-section which is circular, rectangular, square, or any other suitable shape. The tag pusher 130 may have a cross-section which corresponds to the interior cross-section of the blunt tip portion 104. The tag pusher 130 may be fabricated from metal, plastic, or any other suitable material. The stylet pusher 132 may be a hollow member and the tag pusher may at least partially extend into the stylet pusher 132. The stylet pusher 132 may be formed of a tube which may have an inner cross-section which corresponds to the cross-section of the tag pusher 130. For example, if the tag pusher has a circular cross-section, then the interior cross-section of the stylet pusher 132 may also have a circular cross-section. The stylet pusher 132 may be fabricated from metal, plastic, or any other suitable material for such applications. In various embodiments, a compression member 134 may be retained between the proximal end 112 of the blunt tip portion 104 and the distal end 136 of the stylet pusher 132. The tag pusher 130 may pass through the compression member 134. The compression member 134 may be a coil spring (as shown in FIGS. 8A-8B), a leaf spring, or any other suitable compression member.

In various embodiments, the compression member 134 may apply a predetermined compression force to bias the blunt tip portion 104 to the shielding position. As discussed above, the blunt tip portion 104 can move to the compressed, or retracted, position when the blunt tip portion 104 is pushed against tissue with a force greater than the compression force, such that the needle portion 102 can penetrate tissue. Once the needle portion 102 has penetrated through the tissue, the blunt tip portion 104 can immediately extend to the shielding position to help prevent accidental injury to nearby anatomical structures. In addition, once the needle portion 102 has penetrated the tissue, the tag pusher 130 may be fired and a suture anchor 118 may be ejected from the exit port 120. The firing of the tag pusher 130 may be accomplished through the use of an actuator (not shown) located on the handle of the surgical instrument. A physician, or any other operator of the surgical instrument, may operate the actuator to fire the tag pusher 130 to deploy the suture anchor 118 into the tissue, thereby attaching suture 122 to the tissue. When the tag pusher 130 is fired, the tag pusher 130 translates distally inside of the blunt tip portion 104 and ejects a suture anchor 118 from the exit port 120. The compression member 134 may be fabricated from metal, plastic, or any other suitable material for such applications.

Figure 9A:
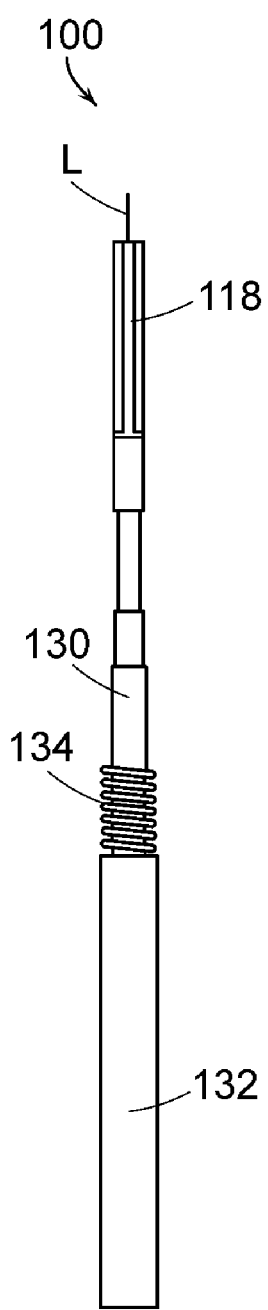
FIG. 9A is a front view of the suture anchor applicator of FIG. 8A with a blunt tip portion removed.
Figure 9B:
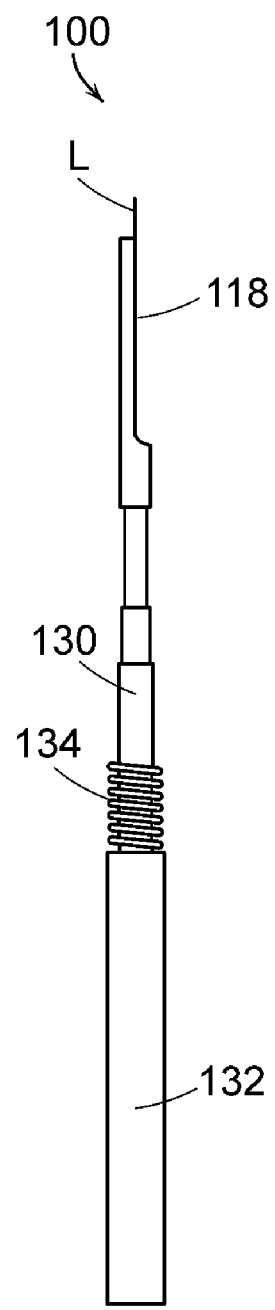
FIG. 9B is a side view of the suture anchor applicator of FIG. 8B with the blunt tip portion removed.
Figure 9C:
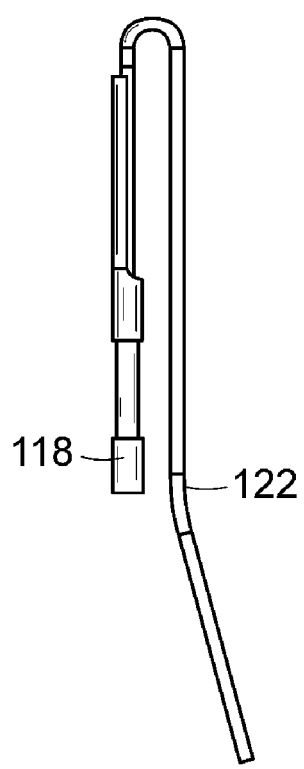
FIG. 9C is a side view of a suture anchor with a suture attached to the suture anchor.
Figure 9D:
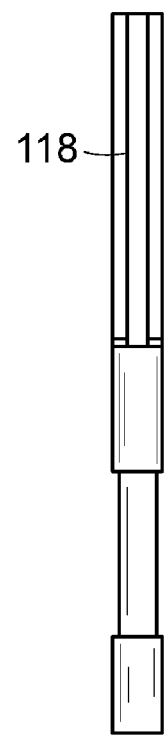
FIG. 9D is a front view of the suture anchor of FIG. 9C.

FIG. 9A is a front view of the suture anchor applicator 100 with a blunt tip portion 104 removed. FIG. 9B is a side view of the suture anchor applicator 100 with the blunt tip portion 104 removed. FIG. 9C is a side view of the suture anchor 118 with the suture 122 attached to the suture anchor 118. FIG. 9D is a front view of the suture anchor 118. As shown in FIGS. 9A-9B, the suture anchor 118 may be located within the blunt tip portion 104. The suture anchor 118 may be located at the distal end 138 of the tag pusher 130. As shown in FIG. 9C, the suture 122 may be attached to the suture anchor 118 at or near the center attachment portion 140 of the suture anchor 118. The suture 122 may be attached to the suture anchor 118 through fusing, gluing, knotting or any other suitable attachment method.

Figure 10A:
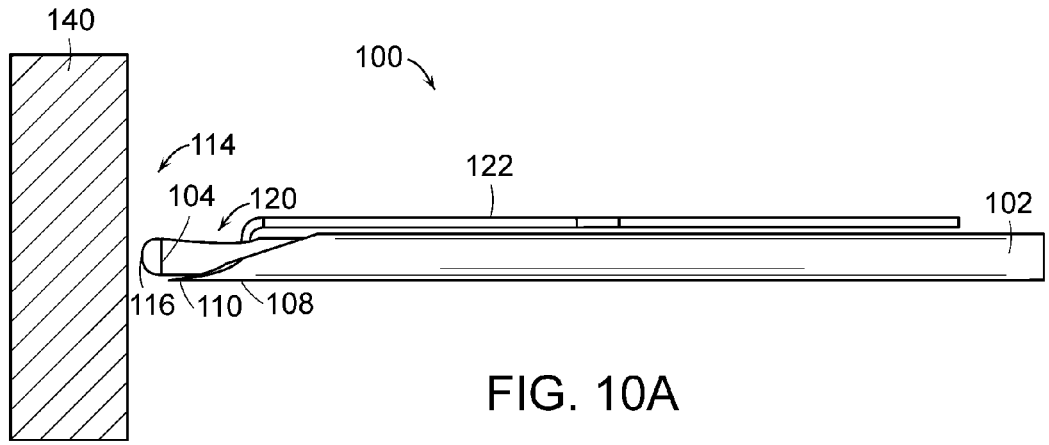
FIGS. 10A-10E illustrate a method of attaching a suture anchor to the tissue of patient using the suture anchor applicator of FIG. 6A.
Figure 10B:
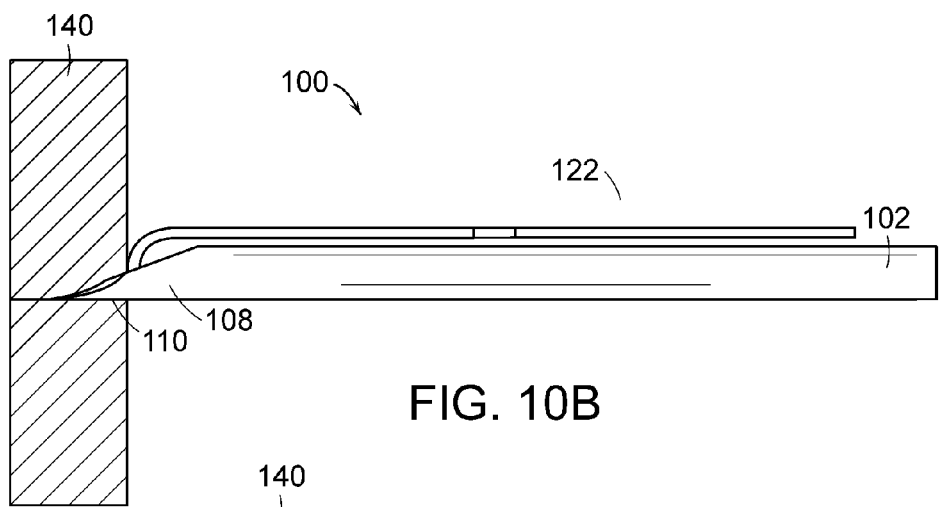
Figure 10C:
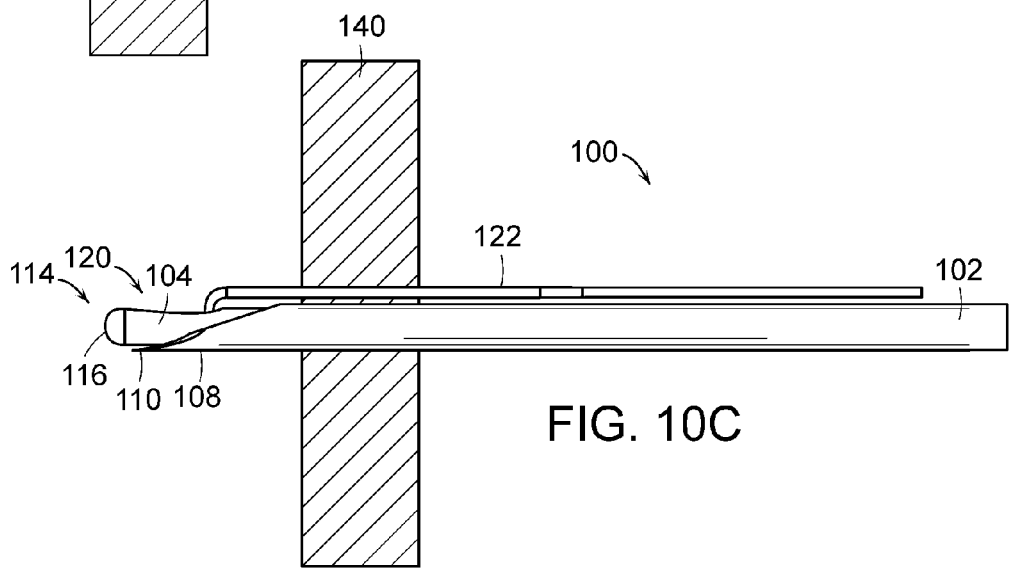
Figure 10D:
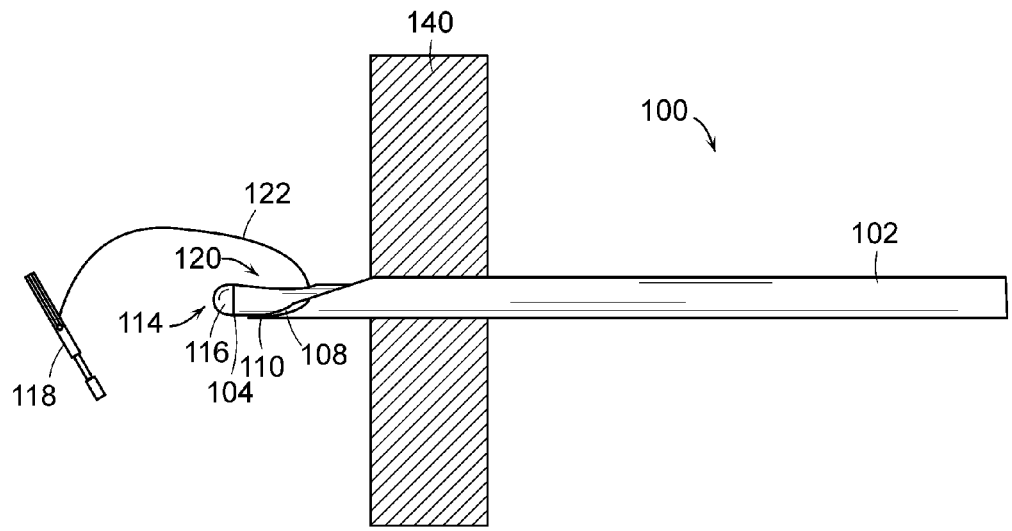
Figure 10E:
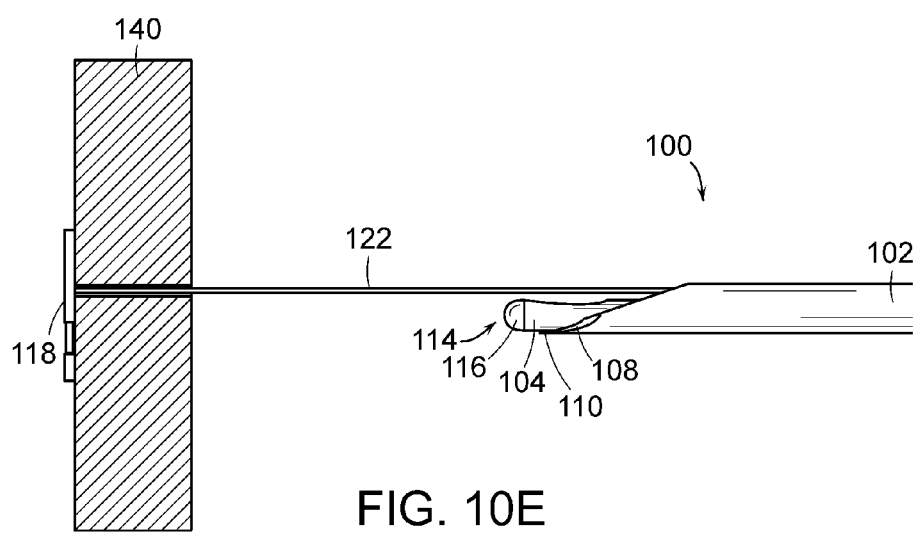

FIGS. 10A-10E illustrate a method of attaching a suture anchor to 118 the tissue 140 of a patient using the suture anchor applicator 100. As shown in FIG. 10A, the blunt tip portion of the suture anchor applicator 100 may be placed against tissue 140 of a patient. In various embodiments, the blunt tip portion 104 may extend past the distal end of the needle portion 102 in the shielding position. As the suture anchor applicator 100 is pushed against the tissue 140, the blunt tip portion 104 contacts the tissue 140 before the needle portion 102. As the blunt tip portion 104 is pushed against the tissue 140, the blunt tip portion 104 may retract into the needle portion 102. As shown in FIG. 10B, the blunt tip portion 104 may be substantially within the needle portion 102 as the needle portion 102 penetrates the tissue 140. As shown in FIG. 10C, once the needle portion 102 has penetrated the tissue 140, the blunt tip portion 104 may be sprung from the needle portion 102 due to the interaction of the blunt tip portion 104 and the compression member 134. As shown in FIG. 10D, an operator of the surgical instrument may operate the actuator to fire the tag pusher 130 (not shown) to deploy the suture anchor 118 to the distal side of the tissue 140. As shown in FIG. 10E, the needle portion 102 and the blunt tip portion 104 may be removed from the tissue 140. The suture anchor 118 may be pulled securely against the distal side of the tissue 140 as the needle portion 102 and the blunt tip portion 104 are removed. The above process may be repeated to attach a second suture anchor 118 to the distal side of the tissue 140. Once the second suture anchor 118 has been placed on the distal side of the tissue 140, the suture 122 may be tightened through the use of a knotting element (not shown) or any other suitable element used for tightening sutures.

Figure 11A:
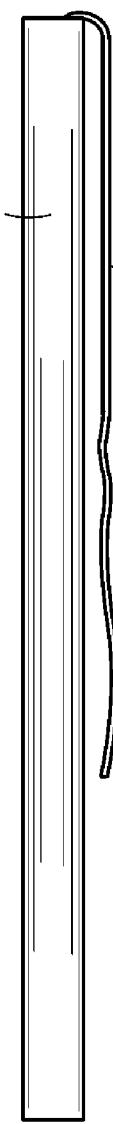
FIG. 11A is a side view of an alternative embodiment of a suture anchor applicator.
Figure 11B:
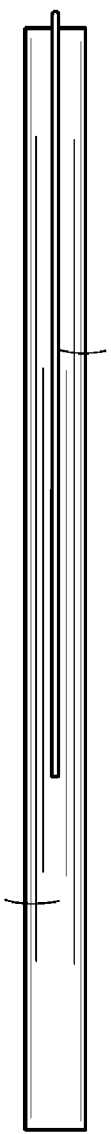
FIG. 11B is a front view of the suture anchor applicator of FIG. 11A.

FIG. 11A is a side view of an alternative embodiment of a suture anchor applicator 200. FIG. 11B is a front view of the suture anchor applicator 200. As shown in FIGS. 11A-11B, the suture anchor applicator 200 may comprise an outer sheath 201. The outer sheath 201 may be formed of a tube which may have a channel extending from the proximal end of the outer sheath 201 to the distal end of the outer sheath 201. The outer sheath 201 may be formed from an extruded polymer, a helically wound metallic wire or from any other suitable materials well-known in the art. A suture 222 may extend proximally from the distal end of the outer sheath 201 along the outside of the outer sheath 201 towards the proximal end of the surgical instrument.

Figures 12A, 12B, 12C:
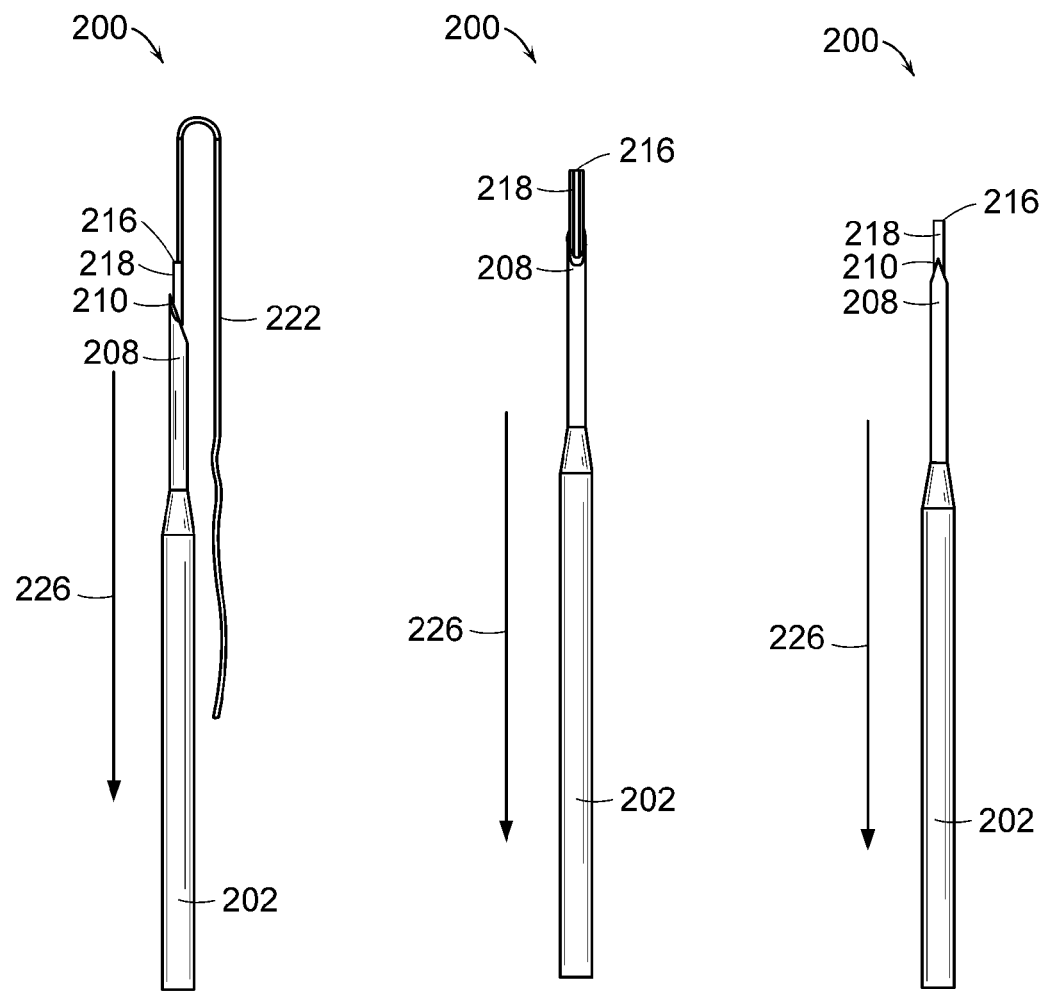
FIG. 12A is a side view of the suture anchor applicator of FIG. 11A with an outer sheath removed.
FIG. 12B is a front view of the suture anchor applicator of FIG. 11B with the outer sheath removed.
FIG. 12C is a rear view of the suture anchor applicator of FIG. 11B with the outer sheath removed.

FIG. 12A is a side view of the suture anchor applicator 200 with the outer sheath 201 removed. FIG. 12B is a front view of the suture anchor applicator 200 with the outer sheath 201 removed. FIG. 12C is a rear view of the suture anchor applicator 200 with the outer sheath 201 removed. As shown in FIGS. 12A-12C, the suture anchor applicator 200 may further comprise a needle portion 202, and a suture anchor 218. At least a portion of the outer sheath 201 may be adapted to slidably retain the needle portion 202. In one embodiment, the tip 216 of the suture anchor 218 may have a substantially flat shape. In other embodiments (not shown), the tip 216 have a blunt shape or other suitable shape.

The needle portion 202 and the suture anchor 218 are shown in FIGS. 12A-12C in a shielding position with the tip 216 of the suture anchor 218 extending distally past the needle portion 204. This may allow the tip 216 of the suture anchor 218 to contact tissue prior to the needle portion 102 contacting the same tissue. In operation, the suture anchor 218 may be pressed against a portion of tissue such that the tip 216 of the suture anchor 218 contacts the tissue. As the force applied to the tip 216 of the suture anchor 218 by the tissue is increased, the suture anchor 218 may slidably retract into the needle portion 202, as shown by arrow 226, until the needle portion 202 punctures the tissue and removes the force placed on the suture anchor 218. Once the needle portion 202 has punctured the tissue, the suture anchor may spring past the shielding position, eject from the needle portion 202 and be deployed on the distal side of the tissue.

In various embodiments, the needle portion 202 may be formed of a tube which may have a channel extending from a proximal end 206 of the needle portion 202 to a distal end 208 of the needle portion 202. The distal end 208 of the needle portion 202 may comprise a tissue penetrating tip 210. The needle portion 202 may be ground to form the tissue penetrating tip 210. The needle portion 202 may be fabricated from stainless steel hypodermic tubing or any other suitable material which may include metal and/or plastic. Alternatively, the needle portion 202 may be formed from an alternate type of metallic or polymeric tube and attached to a cannulated needle (not shown), such as by bolting, screwing, welding, crimping, gluing or any other suitable method. The needle portion 202 may have a diameter in the range of 10-35 gage. For example, the needle portion 202 may be formed from 19 gage stainless steel hypodermic tubing having an outer diameter of approximately 0.043 inches (1.09 millimeters) and a wall thickness of approximately 0.003 inches (0.076 millimeters). At least a portion of the needle portion 102 may be configured to slidably retain the suture anchor 218.

Figure 13A:
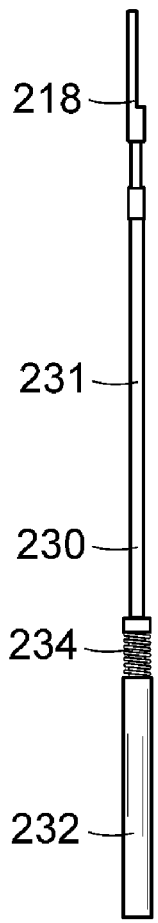
FIG. 13A is a side view of the suture anchor applicator of FIG. 12A with a needle portion removed.
Figure 13B:
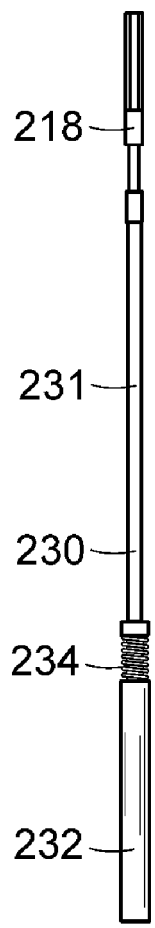
FIG. 13B is a front view of the suture anchor applicator of FIG. 12B with the needle portion removed.

FIG. 13A is a side view of the suture anchor applicator 200 with the needle portion 202 removed. FIG. 13B is a front view of the suture anchor applicator 200 with the needle portion 202 removed. As shown in FIGS. 13A-13B, the suture anchor 218 may be at least partially retained on a tag pusher 230. The tag pusher 230 may extend through at least a portion of the channel of the needle portion 202. The tag pusher 230 may comprise a first member 231, a second member 232, and a compression member 234. In various embodiments, the compression member 234 may be retained between the first member 231 and the second member 232. The first member 231 and the second member may be connected by the compression member 234. The compression member 234 may be attached to the first member 231 and/or the second member 232 through any attachment means which may include bolting, screwing, welding, gluing, fusing, or any other suitable method. The compression member 234 may be a coil spring (as shown in FIGS. 13A-13B), a leaf spring, or any other suitable compression member. The first member 231 and/or the second member 232 may be fabricated to have a cross-section which is circular, rectangular, square, or any other suitable shape. The first member 231 and/or the second member may have a cross-section which corresponds to the interior cross-section of the needle portion 202. The first member 231 and/or the second member may be fabricated from metal, plastic, or any other suitable material for such applications. The compression member 134 may be fabricated from metal, plastic, or any other suitable material for such applications.

In various embodiments, the compression member 234 may apply a predetermined compression force to bias the suture anchor 218 to the shielding position. As discussed above, the suture anchor 218 can move to the compressed, or retracted, position when the suture anchor 218 is pushed against tissue with a force greater than the compression force, such that the needle portion 202 can penetrate tissue. Once the needle portion 202 has penetrated through the tissue, the suture anchor 218 may spring forward and be ejected from the distal end 208 of the needle portion 202 on the distal side of the tissue. The ejection of the suture anchor 218 may be accomplished due to the interaction of the first member 231 and the compression member 234 with the suture anchor. The suture anchor 218 may be press fit into the needle portion 202 to be at least partially retained in the needle portion 202. The springing action of the suture anchor 218 may be sufficient to overcome forces created by the press fit and eject the suture anchor 218 from the needle portion 202.

Figure 14A:
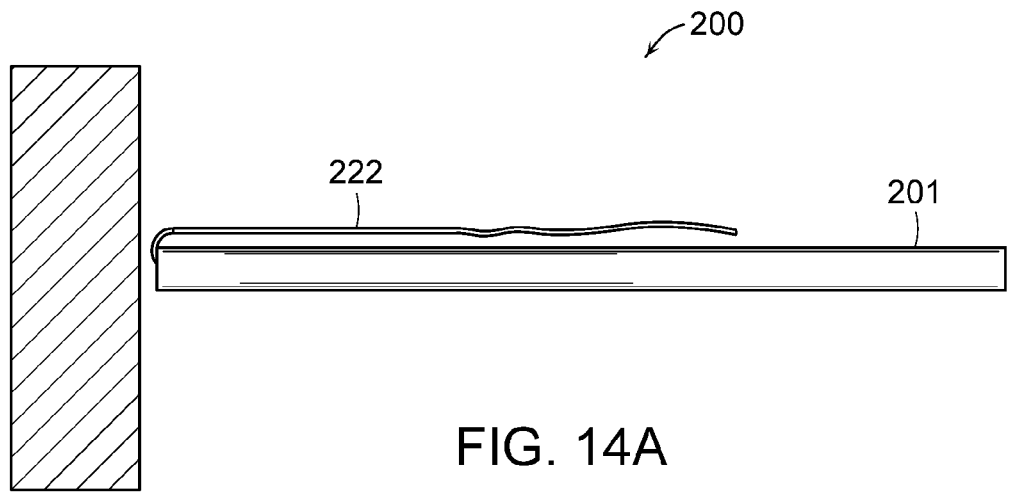
FIGS. 14A-14E illustrate a method of attaching a suture anchor to the tissue of patient using the suture anchor applicator of FIG. 11A.
Figure 14B:
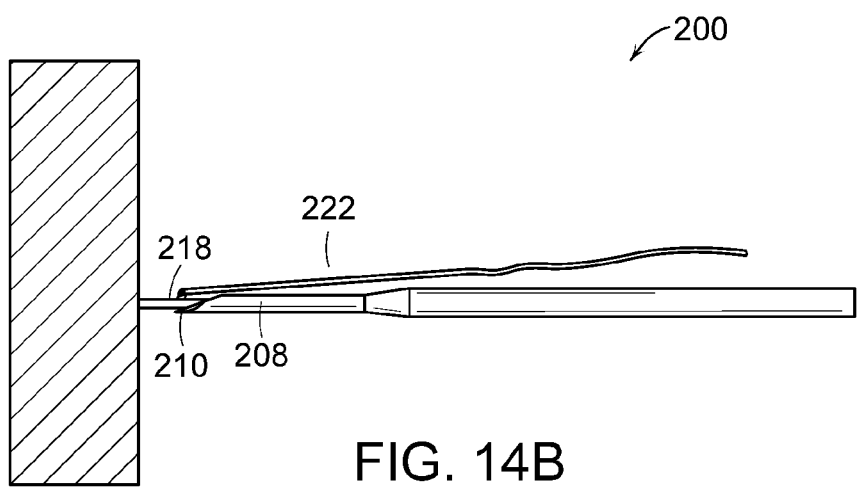
Figure 14C:
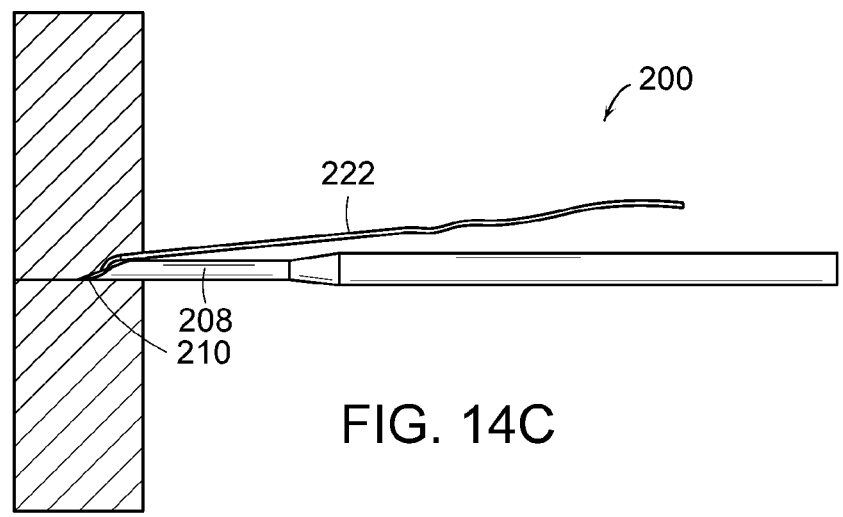
Figure 14D:
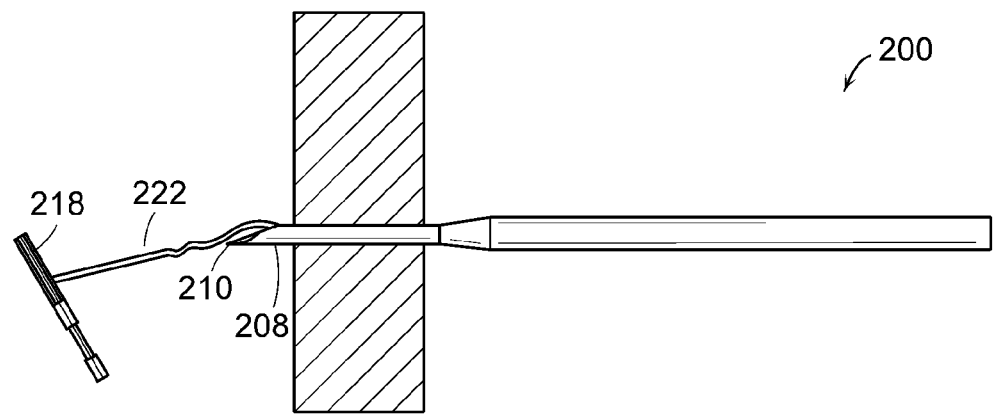
Figure 14E:
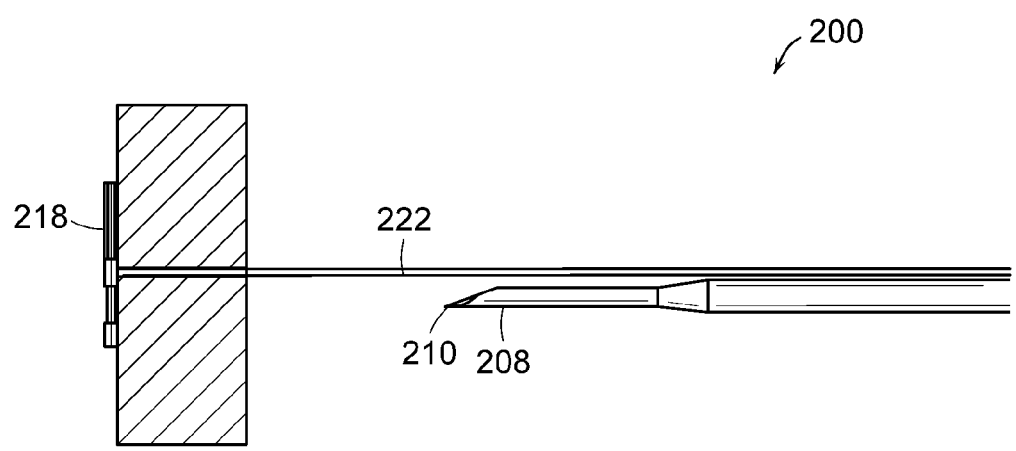

FIGS. 14A-14E illustrate a method of attaching a suture anchor 218 to the tissue of a patient using the suture anchor applicator 200. As shown in FIG. 14A, the outer sheath 201 of the suture anchor applicator 200 may be placed against tissue 240 of a patient. The outer sheath 201 may be retracted once it is placed near the tissue 240 to be sutured. For clarity, the outer sheath 210 has been removed from FIGS. 14B-14E. As shown in FIG. 14B, the suture anchor 218 may extend past the distal end of the needle portion 202 in the shielding position. As the suture anchor applicator 200 is pushed against the tissue 240, the suture anchor 218 contacts the tissue 240 before the needle portion 202. As the suture anchor 218 is pushed against the tissue 240, the suture anchor 218 may retract into the needle portion 202. As shown in FIG. 14C, the suture anchor 218 may be substantially within the needle portion 202 as the needle portion 202 penetrates the tissue 240. As shown in FIG. 14D, once the needle portion 202 has penetrated the tissue 240, the suture anchor 218 may be sprung from the needle portion 202 due to the interaction of the suture anchor 218, the first member 231, and the compression member 234 and be deployed on the distal side of the tissue 240. As shown in FIG. 14E, the needle portion 202 may be removed from the tissue 240. The suture anchor 218 may be pulled securely against the distal side of the tissue 240 as the needle portion 202 is removed. The above process may be repeated to attach a second suture anchor 218 to the distal side of the tissue 240. Once the second suture anchor 218 has been placed on the distal side of the tissue 240, the suture 222 may be tightened through the use of a knotting element (not shown) or any other suitable element used for tightening sutures.

Figure 15:
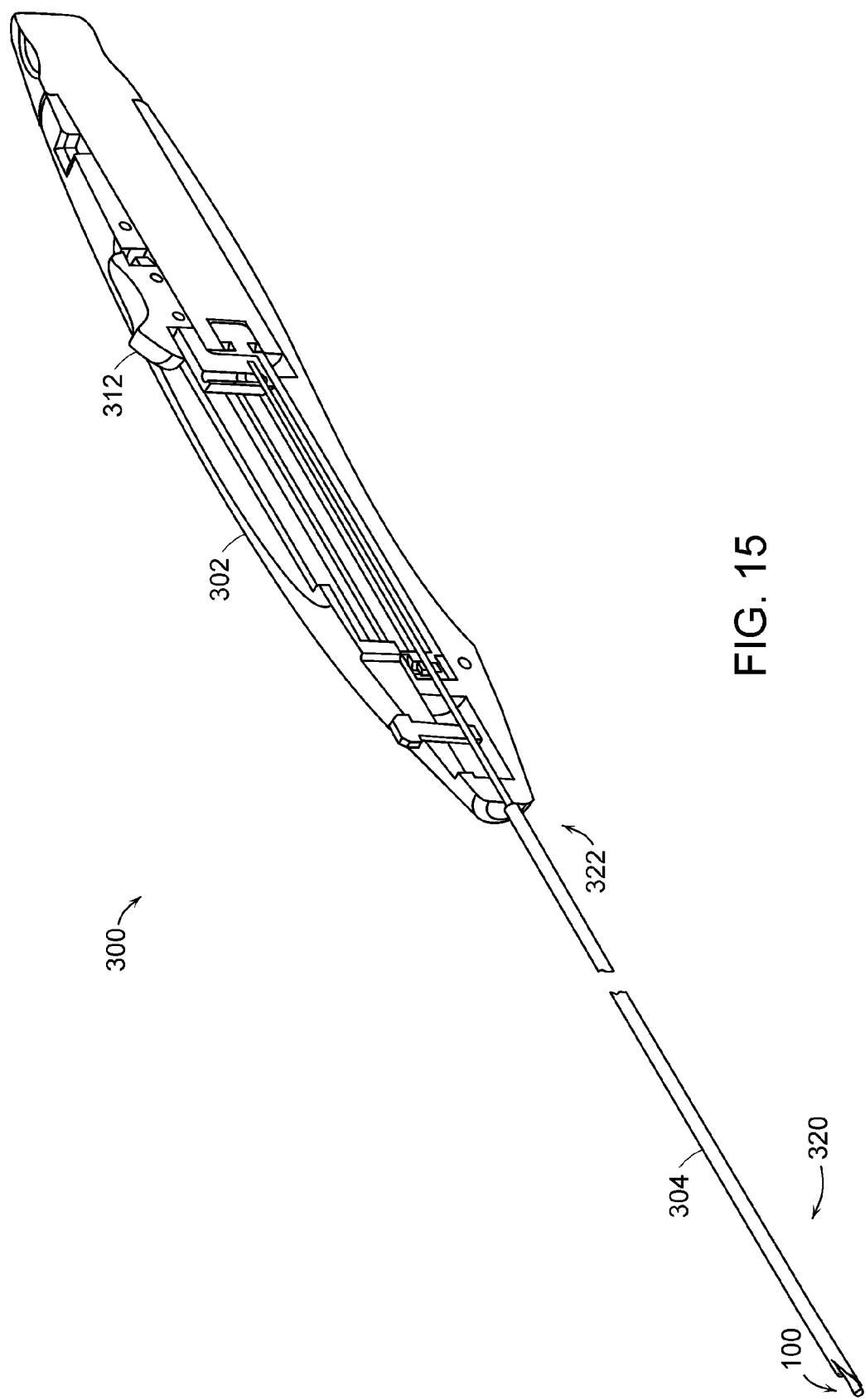
FIG. 15 is a perspective view of an embodiment of a surgical instrument that is adapted to help prevent injury to nearby anatomical structures while deploying a suture anchor.

FIG. 15 is a perspective view of an embodiment of a surgical instrument, generally designated 300, that is adapted to help prevent injury to nearby anatomical structures while deploying a suture anchor. The surgical instrument 300 may include an elongated shaft 304 attached to a handle 302. The shaft 304 may have a distal end 320 and a proximal end 322 defining an axis therebetween. The shaft 304 may be flexible and may be sized for insertion into the working channel of a flexible endoscope. The surgical instrument 300 may be used in conjunction with either of the disclosed suture anchor applicators 100, 200 (not shown). The suture anchor applicators 100, 200 may be located at the distal end 320 of the shaft 304. The suture anchor applicators 100, 200 may be attached to the distal end 320 through any attachment means which may include bolting, screwing, welding, gluing, fusing, or any other suitable method. The surgical instrument 300 is described next as it may be adapted for use with suture anchors 118, 218, although the surgical instrument 300 may also be adapted for use with many types of suture anchors, including any of the suture anchor aspects described herein and their equivalents. As may be seen in FIG. 15, the handle 302 may include an actuator 312. A physician may operate the actuator 312 to deploy a suture anchor into the tissue, thereby attaching a suture to the tissue.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although various embodiments have been described herein, many modifications and variations to those embodiments may be implemented. For example, different types of specimen retrieval bags may be employed. In addition, combinations of the described embodiments may be used. For example, the specimen retrieval bag may comprise a fused portion at the proximal end and an open portion at the distal end. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   a shaft having proximal and distal ends defining an axis therebetween, wherein the shaft is flexible and sized for insertion into a working channel of a flexible endoscope, and wherein the shaft comprises:
   a first tube having a first channel extending from a proximal end of the first tube to a distal end of the first tube, wherein at least a portion of the first tube is adapted to retain a second tube;
   the second tube having a second channel extending from a proximal end of the second tube to a distal end of the second tube, wherein the distal end of the second tube is integrally formed into a tissue penetrating tip structured to puncture a tissue wall, and wherein the second channel is adapted to retain at least one suture anchor;
   the suture anchor having a proximal end and a distal end, wherein the suture anchor is movable from a shielding position to a retracted position, wherein the distal end of the suture anchor is proximal to the tissue penetrating tip when the suture anchor is in the retracted position and extends distally past the tissue penetrating tip when the suture anchor is in the shielding position, and wherein the suture anchor is removably deployable from the tissue penetrating tip such that the suture anchor can be pulled against a distal side of the tissue wall as the tissue penetrating tip is removed from the tissue wall; and
   a tag pusher, wherein the tag pusher comprises a first member and a second member connected with a compression member, and wherein the compression member is structured to decompress to allow the suture anchor to move from the retracted position to a position beyond the shielding position to removably deploy the suture anchor from the tissue penetrating tip when the tissue penetrating tip punctures through a tissue wall.

2. The surgical instrument of claim 1, wherein the tag pusher extends at least partially into the second channel.

3. The surgical instrument of claim 1, wherein the suture anchor is retained at a distal end of the tag pusher.

4. The surgical instrument of claim 1, wherein the compression member is structured to compress when a specified amount of force is applied to the suture anchor to allow the suture anchor to move from the shielding position to the retracted position and allow the tissue penetrating tip to puncture the tissue wall.

5. The surgical instrument of claim 4, wherein the compression member enters into a compressed position when the distal end of the suture anchor is pressed against a proximal side of a tissue wall to be penetrated.

6. The surgical instrument of claim 5, wherein compression of the compression member to the compressed position allows the tissue penetrating tip to extend past the suture anchor to puncture tissue at a proximal side of the tissue wall.

7. The surgical instrument of claim 6, wherein the suture anchor is ejected from the second channel to removably deploy the suture anchor at a distal side of the tissue wall once the tissue penetrating tip has punctured the tissue wall.

* * * * *